(12) United States Patent
Schulz et al.

(10) Patent No.: US 7,913,573 B2
(45) Date of Patent: Mar. 29, 2011

(54) ORTHOPEDIC SIMULATOR WITH A MULTI-AXIS SLIDE TABLE ASSEMBLY

(75) Inventors: Bradley D. Schulz, Savage, MN (US); Paul J. Leska, Sr., Chanhassen, MN (US); Dennis J. Willis, Bloomington, MN (US); Harold F. Fahrendorff, Golden Valley, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 1119 days.

(21) Appl. No.: 11/649,962

(22) Filed: Jan. 5, 2007

(65) Prior Publication Data
US 2007/0169572 A1    Jul. 26, 2007

Related U.S. Application Data

(63) Continuation-in-part of application No. 11/335,974, filed on Jan. 20, 2006, now Pat. No. 7,654,150, and a continuation-in-part of application No. 11/332,407, filed on Jan. 13, 2006, now Pat. No. 7,617,744.

(60) Provisional application No. 60/760,595, filed on Jan. 20, 2006.

(51) Int. Cl.
*G01N 3/02* (2006.01)

(52) U.S. Cl. ......................................................... 73/856

(58) Field of Classification Search .................... 73/798, 73/862.08, 794, 865.3, 856, 865.6
See application file for complete search history.

(56) References Cited

U.S. PATENT DOCUMENTS

| | | | |
|---|---|---|---|
| 3,597,967 A | 8/1971 | Drexler et al. | 73/91 |
| 3,658,143 A | 4/1972 | Schwartz | 177/208 |
| 3,937,071 A | 2/1976 | Slota et al. | 73/809 |
| 4,196,635 A | 4/1980 | Zuber et al. | 73/794 |
| 4,318,301 A | 3/1982 | Justice et al. | 73/856 |

(Continued)

FOREIGN PATENT DOCUMENTS

DE         27 28 007         6/1977

(Continued)

OTHER PUBLICATIONS

International Preliminary Report on Patentability PCT/US2007/000796 dated Jul. 15, 2008.

(Continued)

*Primary Examiner* — Lisa M Caputo
*Assistant Examiner* — Octavia Davis
(74) *Attorney, Agent, or Firm* — Deirdre Megley Kvale; Westman, Champlin & Kelly, P.A.

(57) ABSTRACT

An orthopedic simulator including a holder assembly and a slide table is disclosed. The holder assembly is configured to hold a test specimen to supply test loads. In the embodiment shown, the slide table is coupled to the holder assembly and includes a plurality of translation plates movable along a plurality of axis. As shown, the plurality of translation plates include a first translation plate movable along a first axis and a second translation plate movable along a second axis generally transverse to the first axis. In illustrated embodiments, an adjustable screw lock is configured to provide a positive lock to restrict movement or stroke of the first or second translation plates along the first or second axis. As disclosed, movement of the first or second translation plates is biased via a spring assembly for example to simulate the effect of soft tissue.

28 Claims, 28 Drawing Sheets

U.S. PATENT DOCUMENTS

| | | | | |
|---|---|---|---|---|
| 4,428,238 | A | 1/1984 | Tauscher | 73/663 |
| 4,676,110 | A | 6/1987 | Hodo et al. | 73/809 |
| 4,882,677 | A | 11/1989 | Curran | 364/413.02 |
| 5,009,523 | A | 4/1991 | Folger et al. | |
| 5,014,719 | A | 5/1991 | McLeod | 128/774 |
| 5,151,859 | A | 9/1992 | Yoshino et al. | 701/23 |
| 5,259,249 | A | 11/1993 | Fetto | 73/794 |
| 5,324,247 | A | 6/1994 | Lepley | 482/134 |
| 5,327,038 | A | 7/1994 | Culp | 310/306 |
| 5,337,758 | A | 8/1994 | Moore et al. | 600/594 |
| 5,360,016 | A | 11/1994 | Kovacevic | 600/595 |
| 5,403,252 | A | 4/1995 | Leon et al. | 482/5 |
| 5,415,661 | A | 5/1995 | Holmes | 606/69 |
| 5,511,431 | A | 4/1996 | Hinton | 73/806 |
| 5,569,858 | A | 10/1996 | Askea et al. | |
| 5,670,708 | A | 9/1997 | Vilendrer | 73/37 |
| 5,869,328 | A | 2/1999 | Antoci et al. | 435/287.6 |
| 5,936,858 | A | 8/1999 | Arai | 700/30 |
| 5,937,530 | A | 8/1999 | Masson | 33/534 |
| 5,952,582 | A | 9/1999 | Akita | 73/855 |
| 5,959,215 | A | 9/1999 | Ono et al. | 73/798 |
| 5,999,168 | A | 12/1999 | Rosenberg et al. | 345/161 |
| 6,058,784 | A | 5/2000 | Carroll et al. | |
| 6,171,812 | B1 | 1/2001 | Smith et al. | 435/40.52 |
| 6,418,392 | B1 | 7/2002 | Rust et al. | 702/123 |
| 6,447,448 | B1 | 9/2002 | Ishikawa et al. | 600/300 |
| 6,447,518 | B1 | 9/2002 | Krause et al. | 606/80 |
| 6,472,202 | B1 | 10/2002 | Banes | 435/305.1 |
| 6,502,837 | B1 | 1/2003 | Hamilton et al. | 280/5.515 |
| 6,510,740 | B1 | 1/2003 | Behm et al. | 73/708 |
| 6,538,215 | B2 | 3/2003 | Montagnino et al. | 177/25.16 |
| 6,571,373 | B1 | 5/2003 | Devins et al. | 716/5 |
| 6,581,437 | B2 | 6/2003 | Chrystall et al. | 73/7 |
| 6,629,466 | B2 | 10/2003 | Grote et al. | 73/857 |
| 6,645,251 | B2 | 11/2003 | Salehi et al. | |
| 6,659,200 | B1 | 12/2003 | Eppink | 175/61 |
| 6,706,005 | B2 | 3/2004 | Roy et al. | 600/594 |
| 6,715,336 | B1 | 4/2004 | Xu | 73/7 |
| 6,721,922 | B1 | 4/2004 | Walters et al. | 716/1 |
| 6,860,156 | B1 | 3/2005 | Cavallaro et al. | |
| 6,865,954 | B2 | 3/2005 | Zubok et al. | |
| 7,029,475 | B2 | 4/2006 | Panjabi | 606/279 |
| 7,040,177 | B2 | 5/2006 | Zubok et al. | 73/804 |
| 7,131,338 | B2 | 11/2006 | Zubok et al. | 73/804 |
| 7,204,160 | B1 | 4/2007 | Sadegh et al. | 73/862.041 |
| 7,219,555 | B2 | 5/2007 | Salvesen | 73/788 |
| 7,284,446 | B2 | 10/2007 | Zubok et al. | 73/804 |
| 7,333,111 | B2 | 2/2008 | Ng-Thow-Hing et al. | 345/473 |
| 7,357,038 | B2 | 4/2008 | Zubok et al. | 73/804 |
| 7,383,738 | B2 * | 6/2008 | Schulz | 73/781 |
| 7,617,744 | B2 * | 11/2009 | Schulz et al. | 73/865.9 |
| 7,654,150 | B2 | 2/2010 | Schulz et al. | 73/856 |
| 2001/0045941 | A1 | 11/2001 | Rosenberg et al. | 345/161 |
| 2002/0029610 | A1 | 3/2002 | Chrystall et al. | 73/7 |
| 2002/0166387 | A1 | 11/2002 | Grote et al. | 73/857 |
| 2002/0170361 | A1 | 11/2002 | Vilendrer et al. | 73/849 |
| 2003/0029247 | A1 | 2/2003 | Biedermann et al. | 73/768 |
| 2003/0053901 | A1 | 3/2003 | Roy et al. | 414/735 |
| 2003/0110830 | A1 | 6/2003 | Dehdashtian et al. | 73/37 |
| 2004/0019382 | A1 | 1/2004 | Amirouche et al. | 623/18.11 |
| 2004/0019384 | A1 | 1/2004 | Kirking et al. | 623/20.14 |
| 2005/0056099 | A1 | 3/2005 | Zubok et al. | 73/804 |
| 2005/0241404 | A1 | 11/2005 | Salvesen | 73/788 |
| 2007/0169561 | A1 | 7/2007 | Schulz et al. | 73/794 |
| 2007/0169565 | A1 | 7/2007 | Schulz et al. | 73/862.08 |
| 2007/0169566 | A1 | 7/2007 | Schulz et al. | 73/862.08 |
| 2007/0169567 | A1 | 7/2007 | Schulz et al. | 73/862.08 |
| 2007/0169573 | A1 | 7/2007 | Schulz et al. | 73/865.6 |

FOREIGN PATENT DOCUMENTS

| | | |
|---|---|---|
| DE | 44 11 508 A1 | 2/1994 |
| EP | 0 919 201 A1 | 9/1998 |
| GB | 1108652 | 4/1968 |

OTHER PUBLICATIONS

International Search Report/Written Opinion PCT/US2007/00796 mailed Mar. 27, 2008.

Biomechanical Materials Testing Laboratory [online]. Flinders University, Adelaide, Australia, 2003 [retrieved on Aug. 7, 2007]. Retrieved from www,archive.org using the Internet: <URL:http://web.archive.org/web/20030825155452/http://som.flinders,edu.au/FUSA/ORTHOWEB/lab. Htm>. p. 3,para 7,p. 1, para 3,p. 3, para 3, p. 2, para 7, p. 2, para 11; 4 pages.

"Notification of Transmittal of the International Search Report and the Written Opinion of the International Searching Authority, or the Declaration" for related foreign application No. PCT/US/2007/00727 filed Jan. 10, 2007; date of mailing May 8, 2008; 8 pages.

"Notification of Transmittal of the International Search Report and the Written Opinion of the International Searching Authority, or the Declaration" for related foreign application No. PCT/US/2007/00799 filed Jan. 10, 2007; date of mailing Jul. 15, 2008; 8 pages.

"Notification of Transmittal of the International Search Report and the Written Opinion of the International Searching Authority, or the Declaration" for related foreign application No. PCT/US/2007/00797 filed Jan. 10, 2007; date of mailing Feb. 26, 2008; 11 pages.

"Notification of Transmittal of the International Search Report and the Written Opinion of the International Searching Authority, or the Declaration" for related foreign application No. PCT/US/2007/00733 filed Jan. 10, 2007; date of mailing Oct. 1, 2007; 8 pages.

International Preliminary Report on Patentability PCT/US07/00799 dated Aug. 26, 2008; one page.

International Preliminary Report on Patentability PCT/US07/00797 dated Jul. 15, 2008; one page.

International Search Report PCT./US/07/00727 dated Dec. 28, 2004, one page.

International Preliminary Report on Patentability PCT/US07/00727 dated Jul. 15, 2008; one page.

Written Opinion of the International Searching Authority PCT/US07/00727 mailed May 5, 2008; 3 pages.

Prosthetic Knee Tester, 6 Station Knee Simulator [online]. ATMI—Boston, Nov. 6, 2005 [retrieved on Jul. 6, 2007.] Retrieved from the Internet: <URL:http://web.archive.org/web/20051106114417/http://www.amtiweb.com/sim/knee_machine1.htm> Entire document.

PCT International Search Report and Written Opinion of the International Searching Authority, PCT/US2004/040798 dated Jun. 4, 2005; one page.

* cited by examiner

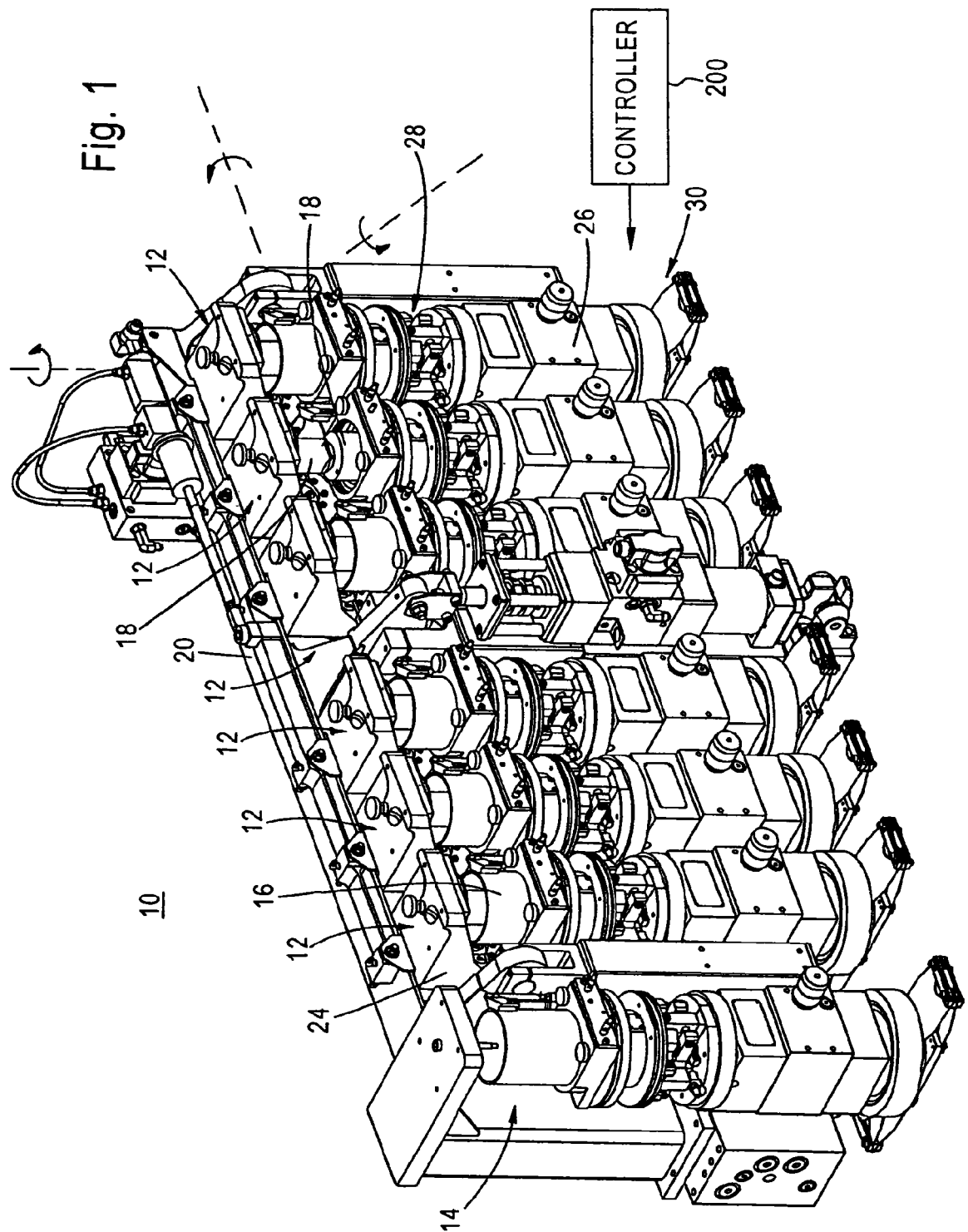

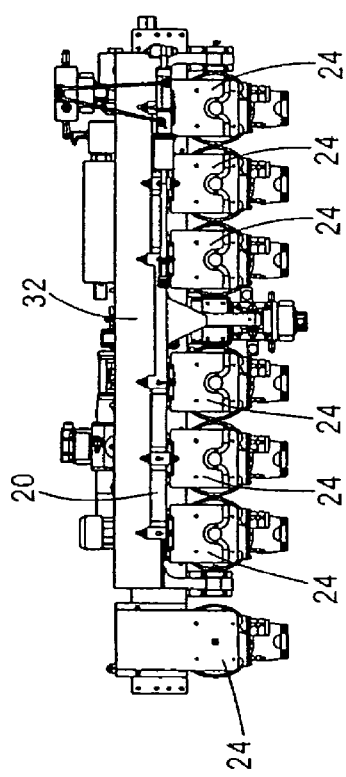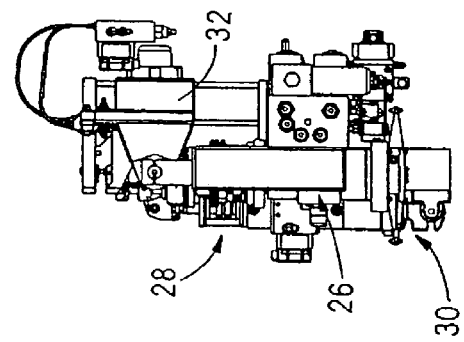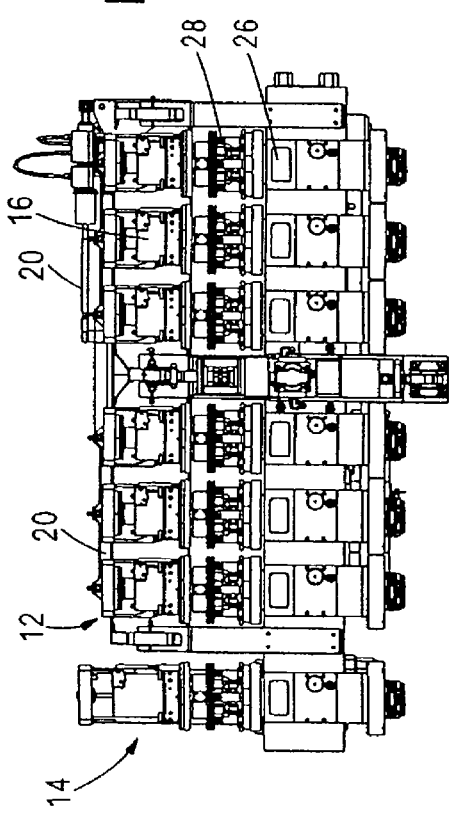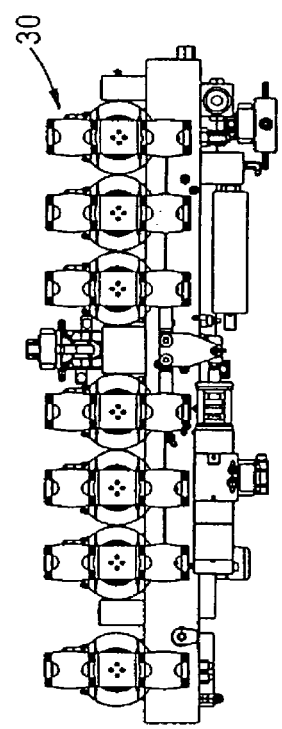

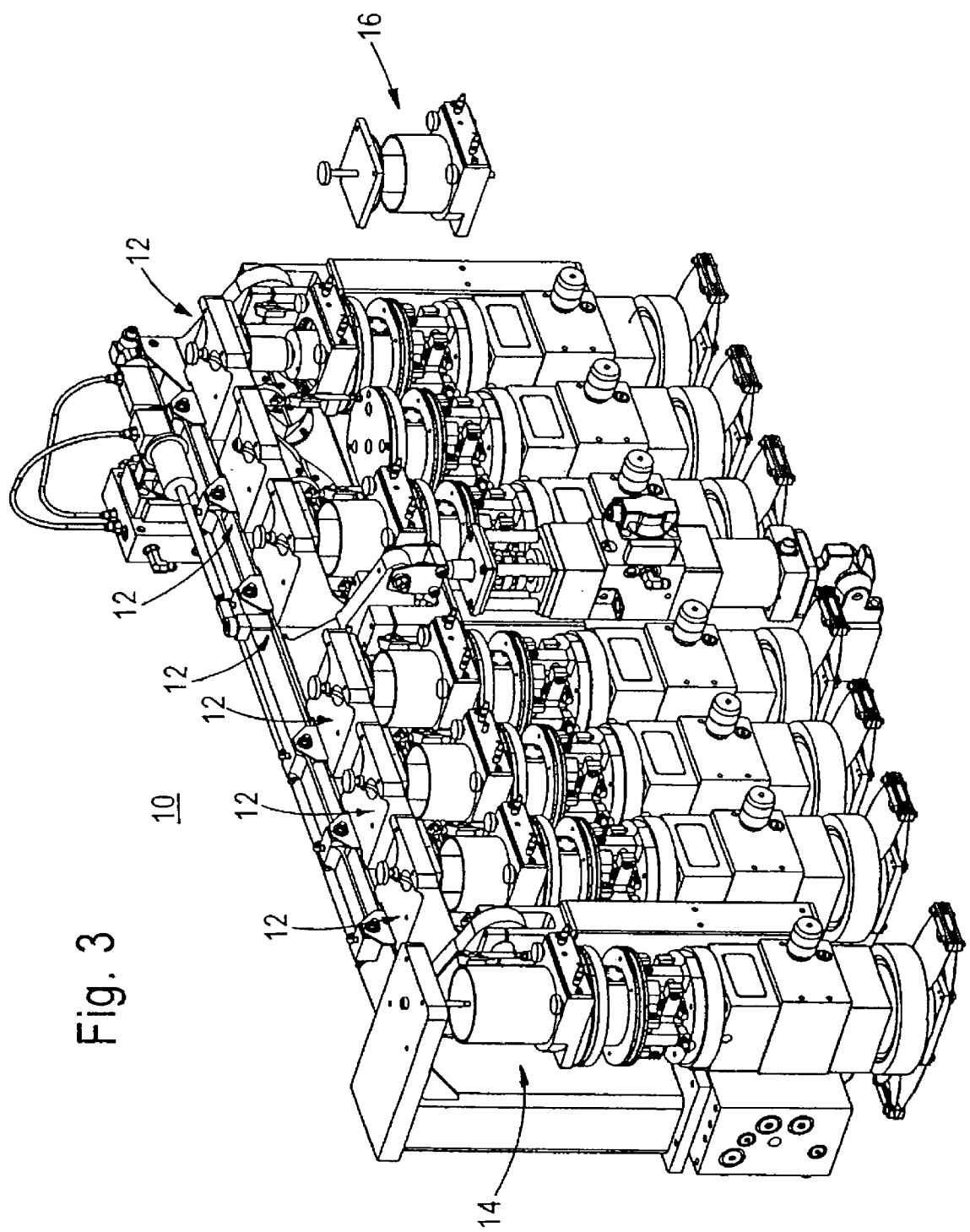

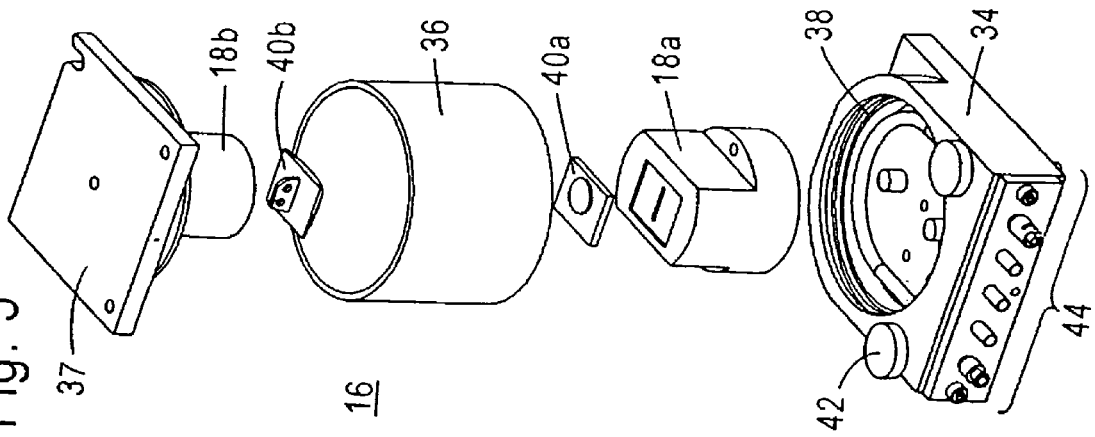
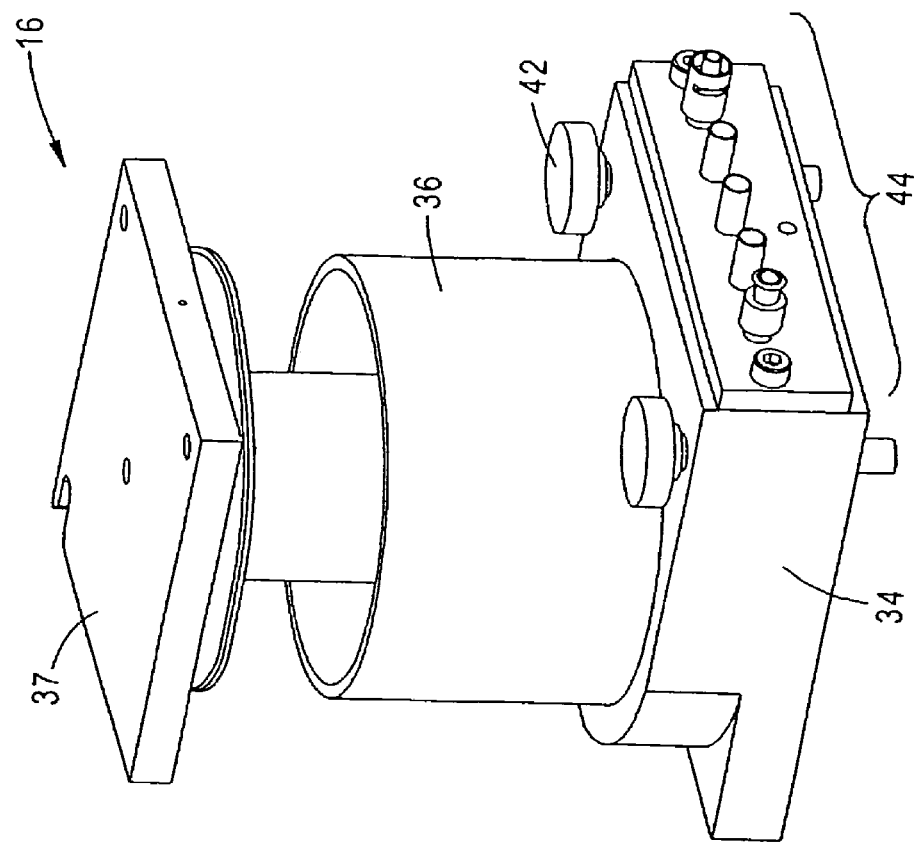

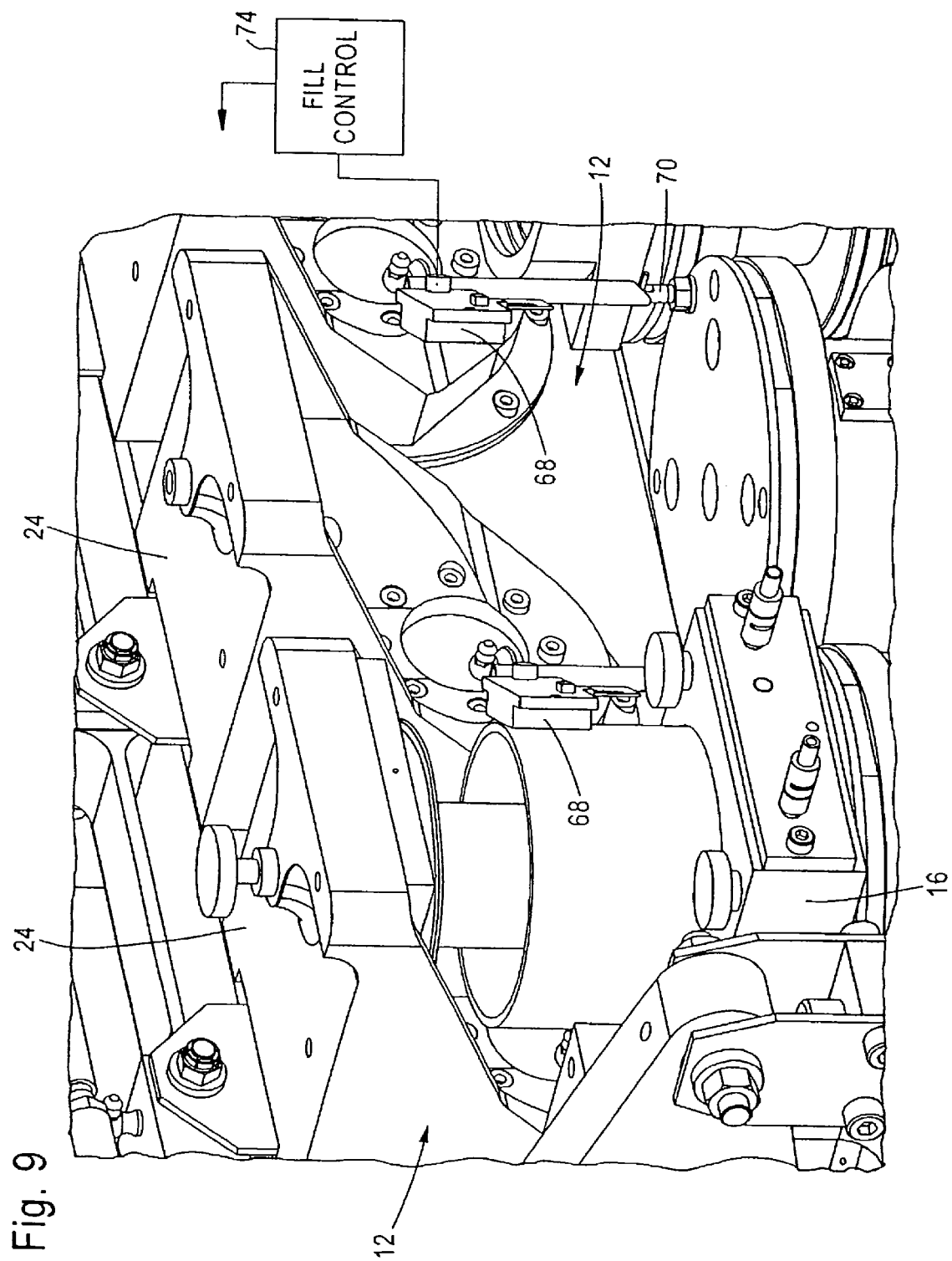

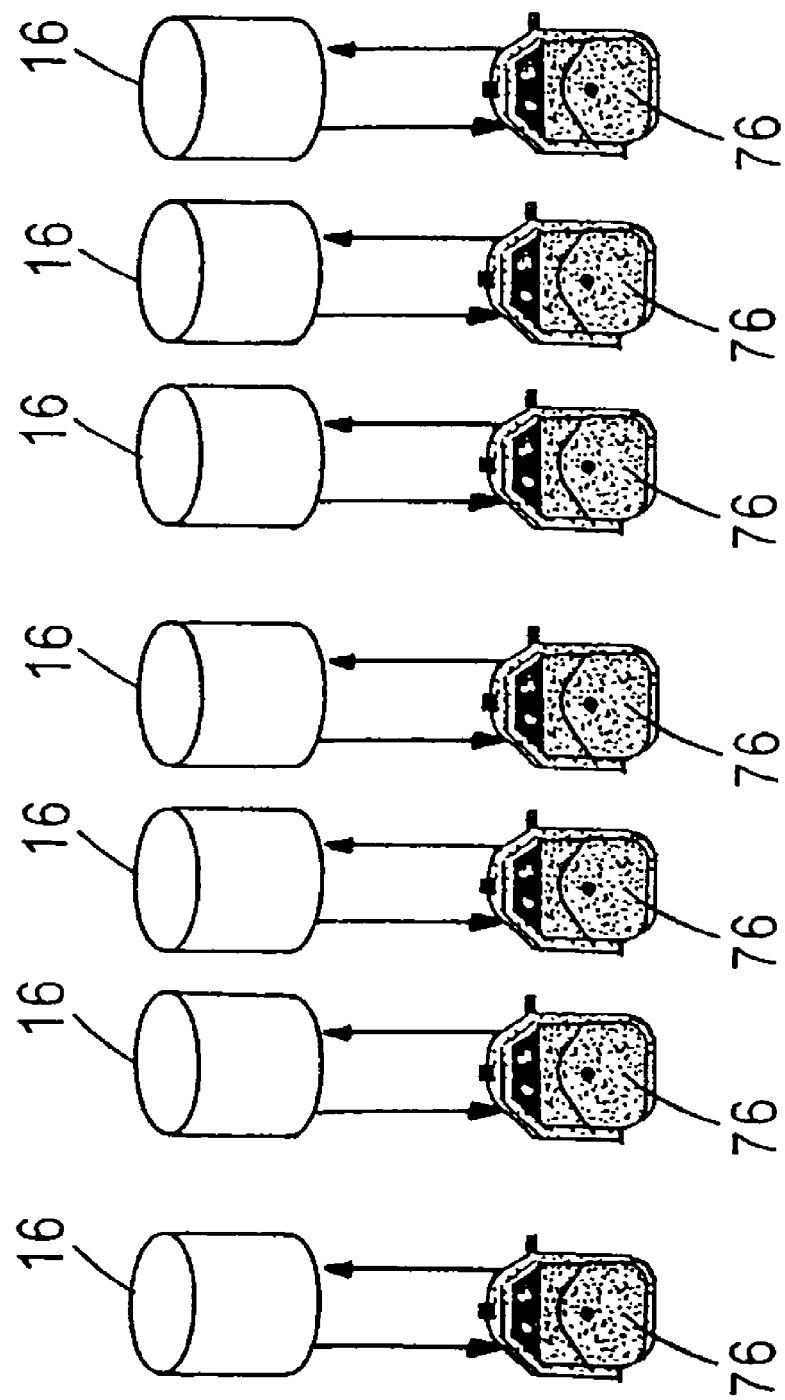

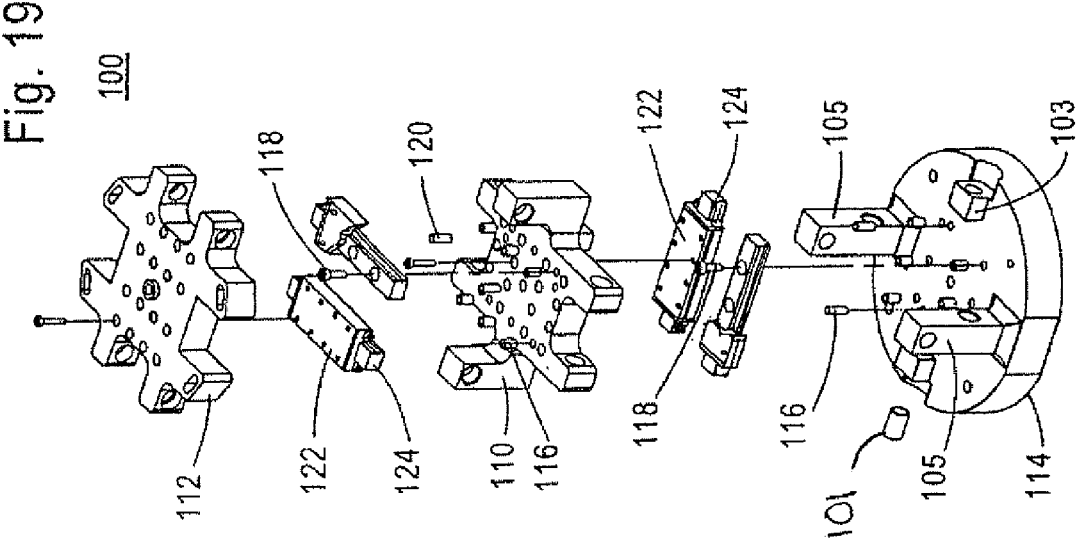

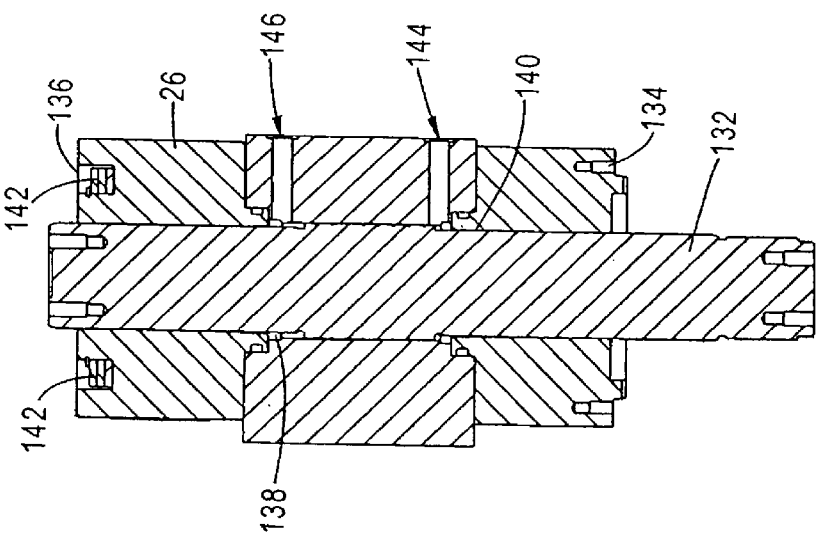
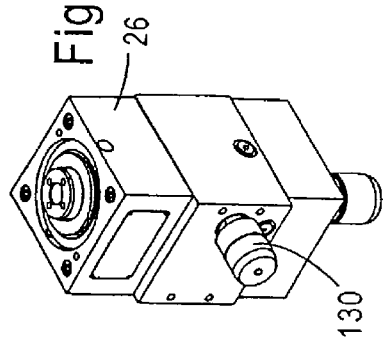
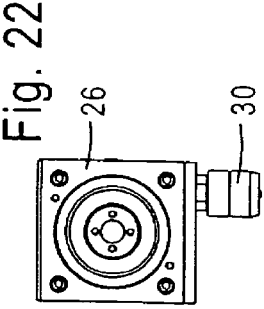
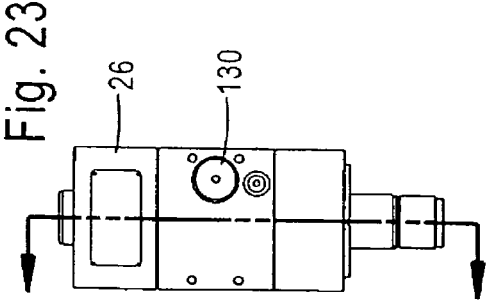

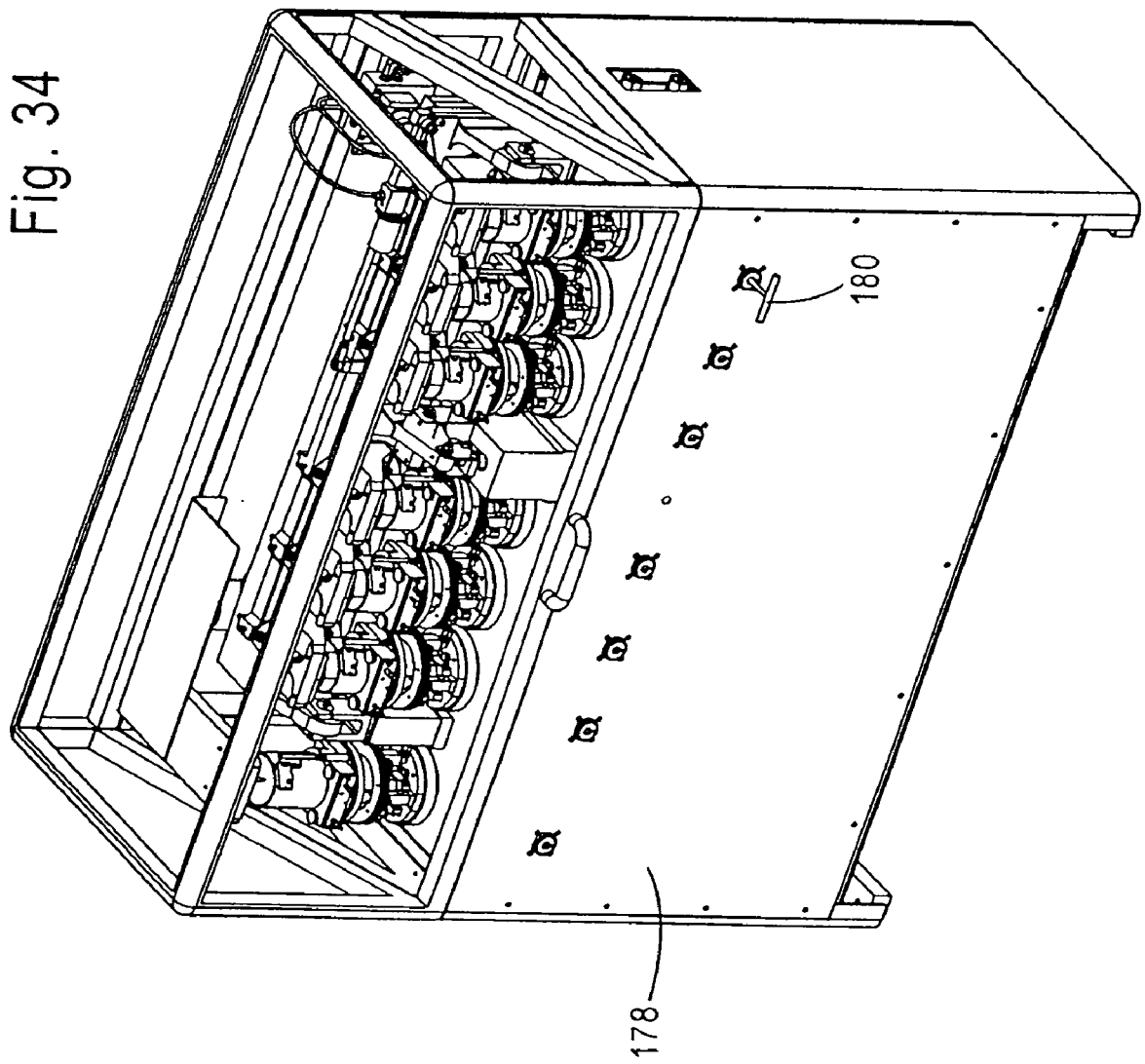

ORTHOPEDIC SIMULATOR WITH A MULTI-AXIS SLIDE TABLE ASSEMBLY

RELATED APPLICATIONS

The present application claims priority to Provisional Patent Application 60/760,595 filed Jan. 20, 2006, U.S. patent application Ser. No. 11/332,407, filed Jan. 13, 2006 and U.S. patent application Ser. No. 11/335,974 filed Jan. 20, 2006 the contents of which are incorporated herein, by reference, in their entirety. This application is a continuation-in-part of U.S. patent application Ser. No. 11/332,407, filed Jan. 13, 2006 now U.S. Pat. No. 7,617,744 and continuation-in-part of U.S. patent application Ser. No. 11/335,974 filed Jan. 20, 2006 now U.S. Pat. No. 7,654,150.

FIELD

There is an ever increasing need for testing of orthopedic devices. Such testing may be required for certification of the devices. For example, wear testing of spinal implants are subject to ISO and ASTM standards. In the example of a spinal wear implant, the test procedure defines the relative angular movement between articulating components, and specifies the pattern of the applied force, speed and duration of testing, sample configuration and test environment to be used for the wear testing of total intervertebral spinal disk prostheses. While the test method focuses on wear testing, additional mechanical tests such as fatigue testing and others can be required.

Spinal implants are only one type of orthopedic device. Others include, for example, hip-joint prostheses, knee-joints, etc. Such devices also need to be tested. For a spinal implant, for example, the testing may be a wear test in which the spinal implant is subjected to forces and loads that are repeated over thousands of cycles. The application of certain motions and forces to a test specimen may involve the use of an "x-y slide assembly" that operates within an orthopedic simulator as a translational assembly. Forces and motions in the "x" and "y" directions, e.g., anterior/posterior and lateral translation motions, may take place in such a slide assembly.

Previous assemblies have employed ball bearings in the slide design, which leads to fretting and skidding when translating. Such fretting and skidding can cause inconsistency between test stations in a simulator with multiple test stations.

SUMMARY

There is a need for an orthopedic simulator that reduces or eliminates fretting and skidding corrosion, and can operate in multiple modes of operation, such as a self-centering free-floating mode, a positive axis lock mode, and a simultaneous shear plane loading mode.

The above stated needs and others are met by embodiments of the present invention which provide an orthopedic simulator comprising a test station configured to hold a test specimen, and a multi-axis slide table on which the test station is mounted for multi-axis movement. The multi-axis slide table includes a bas, a lower translation plate and an upper translation plate. The lower translation plate is mounted to the base by a first linear slide and rail arrangement for movement along a first axis. The upper translation plate is mounted to the lower translation plate by a second linear slide and rail arrangement for movement along a second axis.

The earlier stated needs and others are met by embodiments of the present invention which provide a slide table assembly comprising a base, a first ball-bearing-less linear slide and rail arrangement coupled to the base, and a first translation plate coupled to the base via the first linear slide and rail arrangement for movement relative to the base along a first axis. A second ball-bearing-less linear slide and rail arrangement is coupled to the first translation plate. A second translation plate is coupled to the first translation plate via the second linear slide and rail arrangement for movement relative to the first translation plate along a second axis, different than the first axis.

The foregoing and other features, aspects and advantages of the disclosed embodiments will become more apparent from the following detailed description and accompanying drawings.

BRIEF DESCRIPTION OF THE DRAWINGS

FIG. 1 is a front, perspective view of an orthopedic simulator in accordance with certain embodiments of the invention, with an external housing removed for illustrative purposes, and with forces being schematically depicted.

FIG. 2a is a top view of the orthopedic simulator of FIG. 1; FIG. 2b is a front view; FIG. 2c is a bottom view and FIG. 2d is a side view.

FIG. 3 is a view similar to FIG. 1, illustrating the removability of a specimen containment module.

FIG. 4 depicts an exemplary embodiment of an assembled specimen containment module.

FIG. 5 is an exploded view of the specimen containment module of FIG. 4.

FIG. 9 depicts two test stations, with one test station having a specimen containment module releasably attached thereto.

FIG. 10 schematically depicts an exemplary arrangement for circulating bath fluid.

FIG. 18 is a perspective view of the x-y slide assembly in accordance with embodiments of the present invention.

FIG. 19 is an exploded view of the x-y slide assembly of FIG. 18.

FIG. 21 is a perspective view of an embodiment of an actuator in isolation.

FIG. 22 is a top view of the actuator of FIG. 21

FIG. 23 is a side view of the actuator of FIG. 21.

FIG. 24 is a cross-sectional view of the actuator of FIG. 21.

FIG. 34 depicts the orthopedic simulator within a housing.

DETAILED DESCRIPTION

Figure 6:
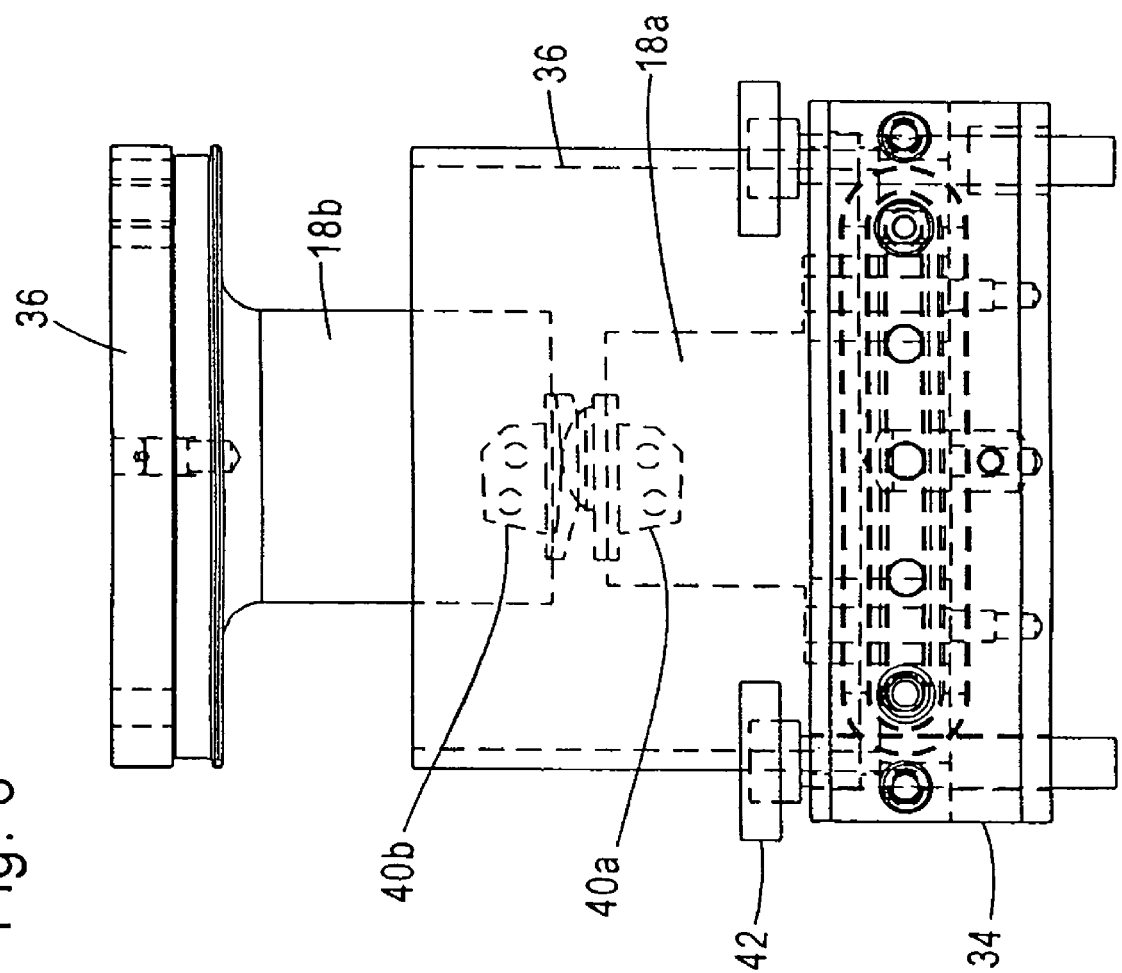
FIG. 6 is a side, partially cross-sectional view of the specimen containment module of FIG. 4.

The orthopedic simulator of the present invention may be employed, for example, as a spinal implant wear test machine. In such a configuration, the intent of ISO 18192 is satisfied. The orthopedic simulator is designed for accuracy as well as increased speed.

In the following description, it is assumed that the orthopedic simulator is a spinal implant wear test machine, but it should be apparent to those of ordinary skill in the art that this is exemplary only. The features, concepts and designs depicted in the following figures and description may be employed in other types of machines and orthopedic simulators.

The embodiments of the present invention address and solve problems related to the translation of a test specimen in an orthopedic simulator and more particularly to fretting and skidding corrosion present in previous translation assemblies, and the provision of multiple operational modes with a single slide table assembly. The embodiments of the invention solve these problems, at least in part, by providing an orthopedic simulator with a test station configured to hold a test specimen, and a multi-axis slide table on which the test station is mounted for multi-axis movement. The multi-axis slide table includes a base, a lower translation plate mounted to the base by a first linear slide and rail arrangement for movement along a first axis and an upper translation plate mounted to the lower translation plate by a second linear slide and rail arrangement for movement along a second axis.

FIG. 1 depicts an orthopedic simulator 10 for testing of test specimens of orthopedic devices. The orthopedic simulator 10 has a plurality of test stations 12. In the illustrated embodiment, there are six test stations 12 in which specimens are subjected to the forces applied by the machine 10, and a control station 14 that holds a specimen that is not subjected to all of the forces provided at the other test stations 12.

The orthopedic simulator 10 is able to provide forces Fx, Fy, and Fz in the x, y and z directions as depicted in FIG. 1, shown with the x, y and z axes at one of the test stations 12. Additionally, torques may be applied around the x, y and z axes, as depicted. The test specimen is not shown in FIG. 1 so as not to obscure the present invention. In the spinal implant wear testing machine according to certain embodiments of the invention, a specimen containment module is provided that contains fluids in which the test specimen is immersed. Upper and lower adapters 18 (only seen clearly at one of the test stations 12 in which the specimen chamber is removed for illustrative purposes) hold the test specimens between them within the specimen containment module 16.

A linkage 20 provides forces in the x direction with the linkage 22 providing forces in the y direction. Gimbals 24 are connected to the upper adapters 18 and may be moved around the y axis and around the x axis to provide moments around the x and y axes.

Vertical loads, represented by forces along the z axis, are provided by vertical load actuators 26, as shown in FIG. 1. Although different types of actuators may be employed, a friction-free axial actuator is preferable to provide for a friction-free axial/torsion actuation system. The vertical load actuator 26 applies a vertical loading along the z axis through components 28 to the test specimen via the lower adapter 18. In the illustrated embodiment, which will be described in more detail later, the components 28 include an x-y slide table and a load cell.

In is desirable to provide a transmission of drive torque with little deflection related error, having high torsional stiffness. At the same time, low axial stiffness is desirable so that there is little cross-talk onto the vertical loading and so the cross-talk is not seen at the load cell. An axial rotation linkage 30 is coupled to the vertical load actuator 26. The motion of the axial rotation linkage 30 is around the vertical axis z, as depicted in FIG. 1. Although the axial rotation linkage 30 is depicted at the bottom of FIG. 1, it should be apparent to those of skill in the art that the structure depicted in FIG. 1 is suspended vertically so that the axial rotation linkages 30 are free to rotate. This will become more apparent in later-described figures.

FIGS. 2a-2d depict alternate views of the orthopedic simulator 10. FIG. 2a is a top view which best shows the arrangement of the linkages 20 with the gimbals 24. A crosshead 32 is provided, which may also best be seen in FIG. 2d. FIG. 2a is a top view, while FIG. 2b is a front view, FIG. 2c is a bottom view and FIG. 2d is a side view.

FIG. 3 depicts a perspective view of the orthopedic simulator of FIG. 1, with a specimen containment module 16 that is remote from the orthopedic simulator 10. The specimen containment modules 16 are releasably attachable to the test station 12. The releasable attachment feature of each of the specimen containment modules 16 enables bench top preparation work on the test specimen to be performed remotely from the environment of the orthopedic simulator 30. This remote loading and preparation capability allows for careful removal and insertion of delicate test specimens. Further, the mounting of one-piece specimens is facilitated with this arrangement. An important consideration is the reduction in the contamination potential created by remotely mounting a specimen within the specimen containment module. The specimen containment module 16 also contains adapters 18 that are designed for flexibility, ease of manufacturing and low cost.

An exemplary embodiment of a specimen containment module 16 is shown in isolation in FIG. 4, and in exploded view in FIG. 5. The specimen containment module contains a base 34 and upper connector 37 that interface to a test station 12 and at which the specimen containment module 16 is releasably attached to the orthopedic simulator 10. A chamber 36, when inserted into the moat 38 in the base 34, forms a fluid container with the base 34. A test specimen 40 is depicted with a lower portion 40*a* and an upper portion 40*b*. However, certain test specimens may also be one-piece specimens.

Releasable fasteners 42, such as thumb screws, may be employed to releasably attach the specimen containment module 16 to the orthopedic simulator 10. Fluid connections 44 are used to provide fluid as will be described in more detail in the following figures.

FIG. 6 is a side, partially cross-sectional view of the specimen containment module 16 of FIGS. 4 and 5. The test specimen 40 is shown with the upper and lower portions coupled together, as seen in FIG. 6.

Figure 7:
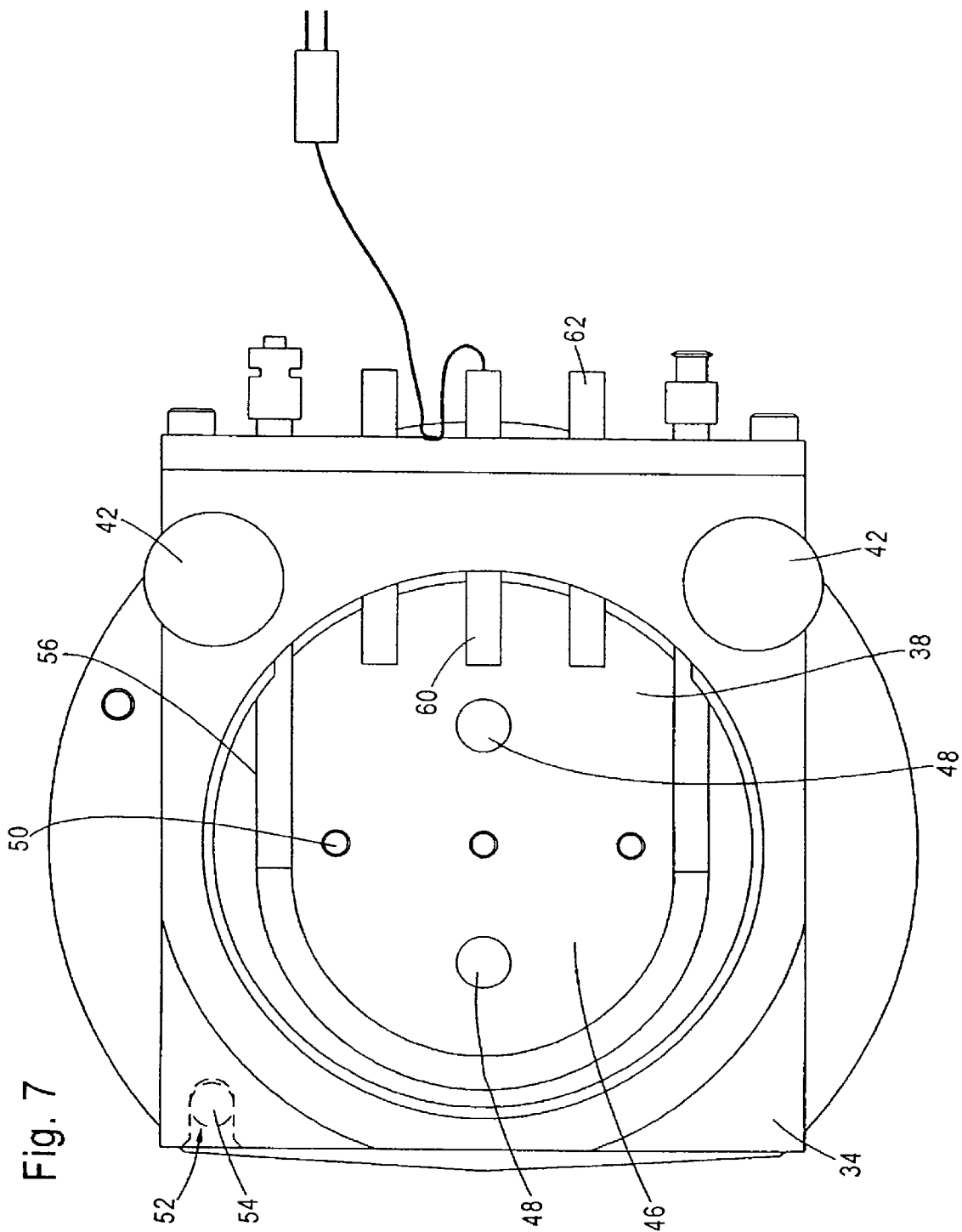
FIG. 7 is a top view of a base of the specimen containment module of FIG. 4.

FIG. 7 is a top view of the base 34. A specimen mounting platform 46 is provided which includes two pins 48, with one pin piloting and another pin interacting with a slot in the lower adapter 18*a* for anti-rotation purposes. Screw holes 50 are depicted and may be employed to provide a specimen hold down function.

The base 34 also includes a recess 52 that is able to interact with a pin 54 on the orthopedic simulator 10. This provides a slidable installation of the specimen containment module 16. A tubing loop 56 is provided within the base to provide a temperature control of the bath in which the test specimen 40 is immersed. As will be described in more detail, a temperature control fluid is circulated through the tubing loop 56 to precisely control the temperature of the bath. The temperature control fluid does not intermix with the bath fluid. A temperature probe 60 provides feedback on the temperature of the bath and can be used to control the temperature control fluid. The signal from the temperature probe 60 is provided as a feedback signal to a heather (not shown in FIG. 7).

Recesses 58 provide for thumb screws or other releasable fasteners to secure the specimen containment module 16 to the orthopedic simulator 10. Bath fluid circulation tubes 62 are used to circulate bath fluid within the fluid container formed by the base 34 and the chamber 36, as will be described in more detail later with respect to FIG. 9.

Figure 8:
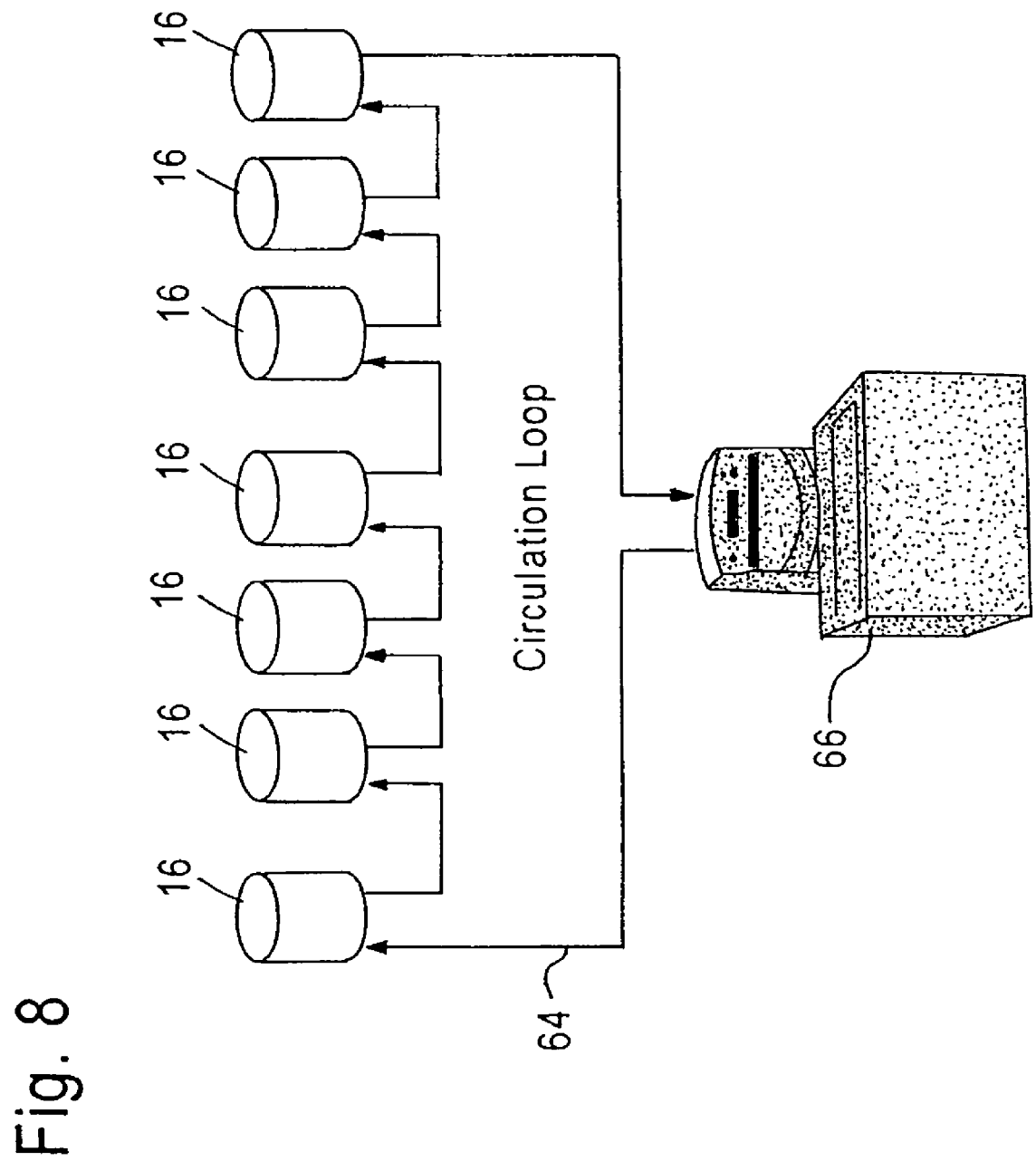
FIG. 8 is a schematic depiction of an embodiment of a circulation loop for circulating a temperature control fluid in a temperature control circuit.

FIG. 8 depicts a circulation loop for circulating the temperature control fluid in the temperature control circuit. The temperature control fluid is circulated in each of the specimen containment modules 16 through the tubing loops 56, seen in FIG. 7. The tubing loops 56 are connected to a single circulation loop 64 that circulates a temperature control fluid, such as water, through the closed loop system. Although water is an exemplary temperature control fluid, other fluids may be employed as a temperature control medium in different embodiments. The tempered water is circulated through the heat exchangers in each of the baths of the specimen containment modules 16. A heater 66 provides a precise control and circulation of the tempered water. The heater 66 receives temperature signals from the temperature probes 60 and employs this information to control the temperature of the temperature control fluid, and hence, the bath in each of the specimen containment modules 16.

Figure 8A:
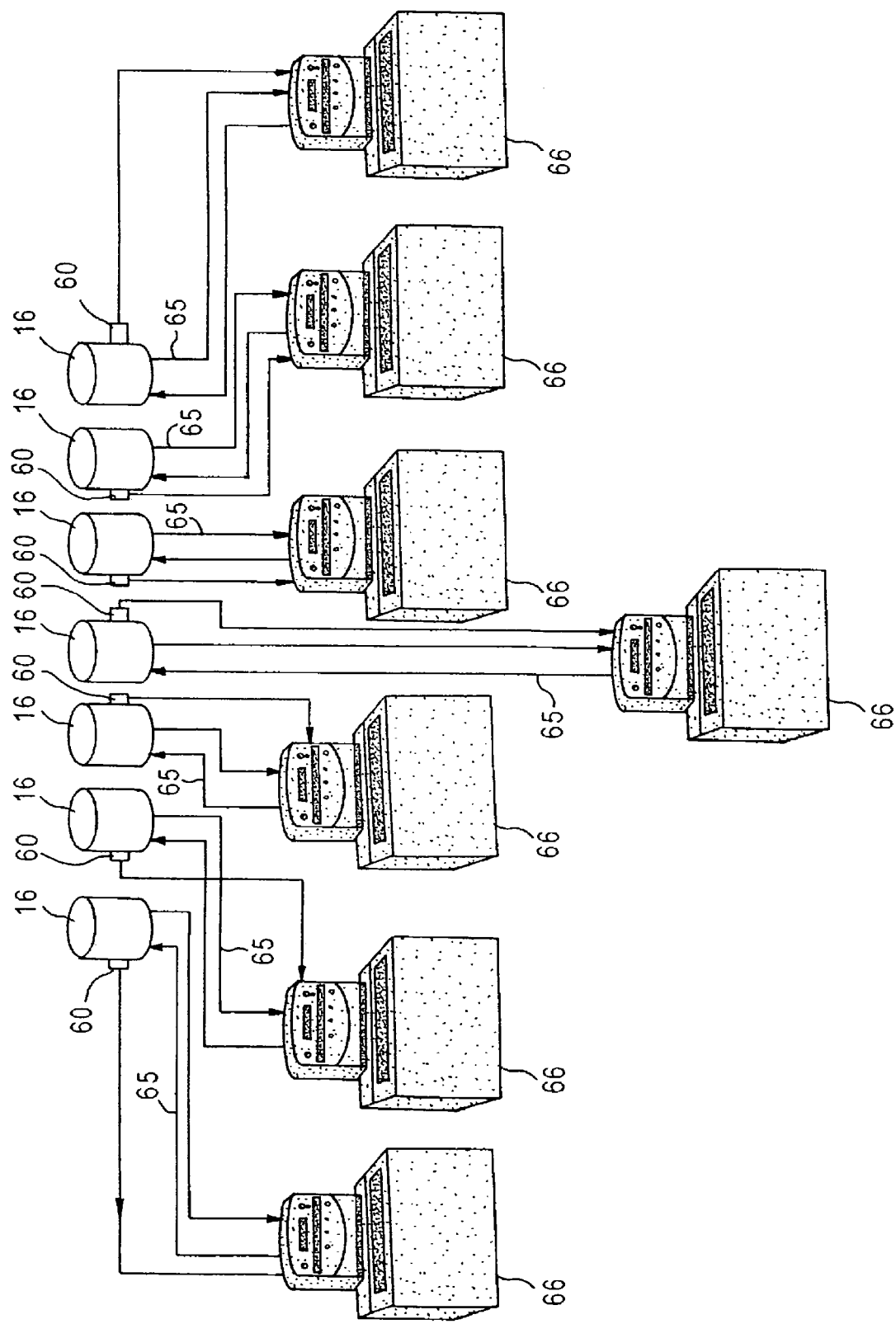
FIG. 8a is a schematic depiction of a temperature control arrangement for circulating temperature control fluid in accordance with another embodiment of the present invention.

The daisy-chained approach depicted in FIG. 8 produces a very stable temperature in each of the baths at the specimen containment modules 16. In addition to stability, a consistency of temperature from station 12 to station 12 is achieved since the entire circulation loop 64 reaches a stabilized temperature. Also, a single heater may be employed, reducing costs, In certain embodiments, such as depicted in FIG. 8*a*, each of the baths of the specimen containment modules 16 may be individually controlled with separate circulation loops 65 for each bath. Each circulation loop 65 has its own heater 66, which receives temperature feedback signals from the respective temperature probe 60. However, the embodiment depicted in FIG. 8 is preferred. The arrangement of FIG. 8*a*, like that of FIG. 8, also has the advantage over electric heating elements or other types of heating, in preventing overtemperature related fluid degradation.

FIG. 9 depicts two test stations 12, one of which has a specimen containment module 16 releasably attached thereto. A non-contact level sensor 68, such as those known in the sensing art, are provided on posts 70 near the chamber 36. The height of the non-contact level sensor 68 may be adjusted along the pillar 70 in the direction of arrow 72. This allows the desired fluid height within the chamber 36 to be precisely adjusted. The non-contact level sensor 68 provides its signals to a fill controller 74, schematically indicated as being connected to a non-contact level sensor 68. The fill control 74, based upon the signals received from the non-contact level sensors 68, determines whether the fluid in the specimen containment module 16 needs to be replenished. The test fluid, such as bovine fluid, for example, may evaporate to some extent, thereby increasing the concentration of the fluid. Distilled water is furnished (through a fill tube, not shown) under the control of the fill control 74.

An arrangement for the circulation of the bath fluid is depicted in FIG. 10. Unlike the temperature control fluid, individual loops are preferred in order to maintain each test specimen and bath in its own environment. In other words, cross-contamination of wear particles is avoided by providing the individual loops for each specimen module. In certain embodiments, peristaltic pumps 76 are employed for each of the individual loops. A stirring action is provided.

Figure 11:
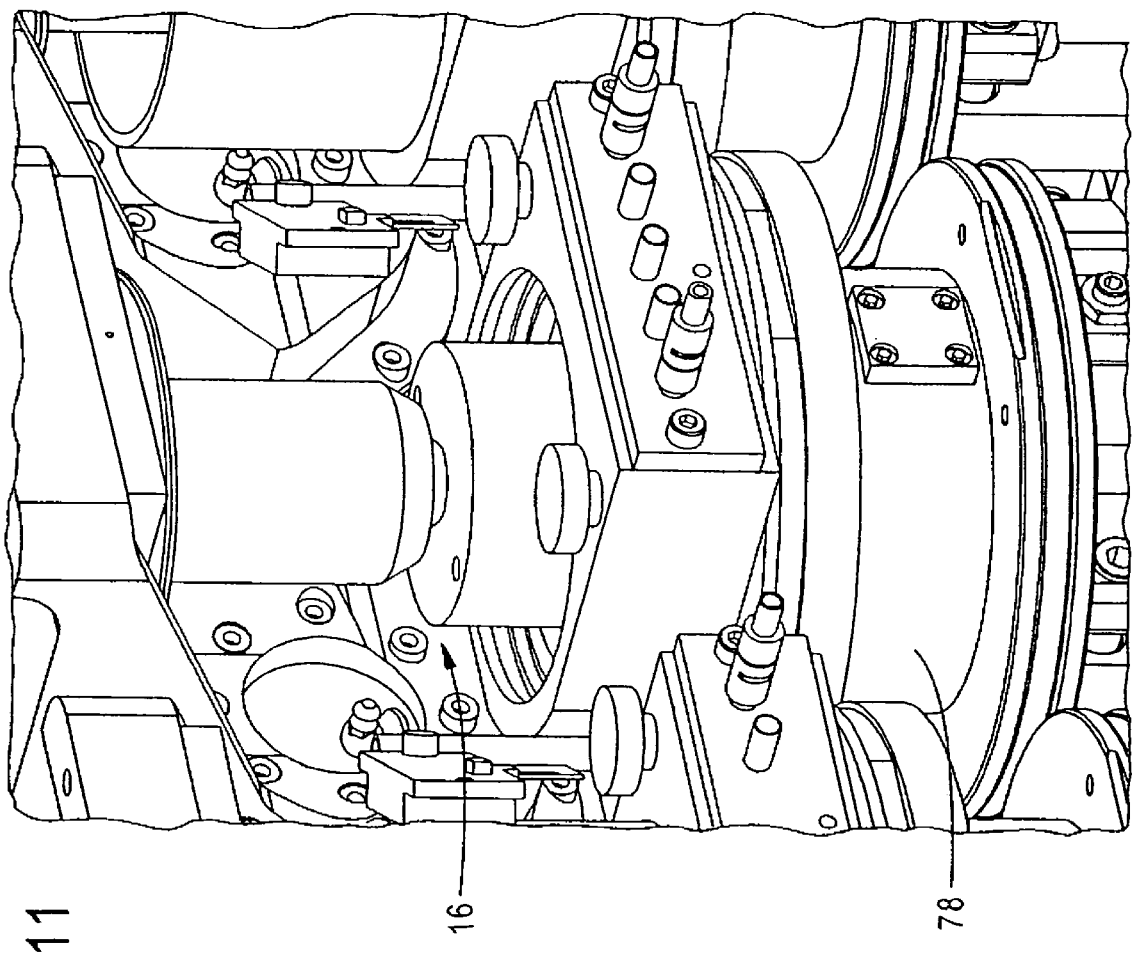
FIG. 11 depicts an embodiment of a specimen containment module in an installed position.

FIG. 11 shows a specimen containment module 16 (without the chamber 36 for illustrative purposes) in an installed position within the orthopedic simulator 10. The specimen containment module is releasably attached at its base 34 to a load cell module 78. The load cell module is designed to accommodate either a single or multi-axis force transducer. In the illustrated embodiment, a single axis transducer is depicted.

Figure 12:
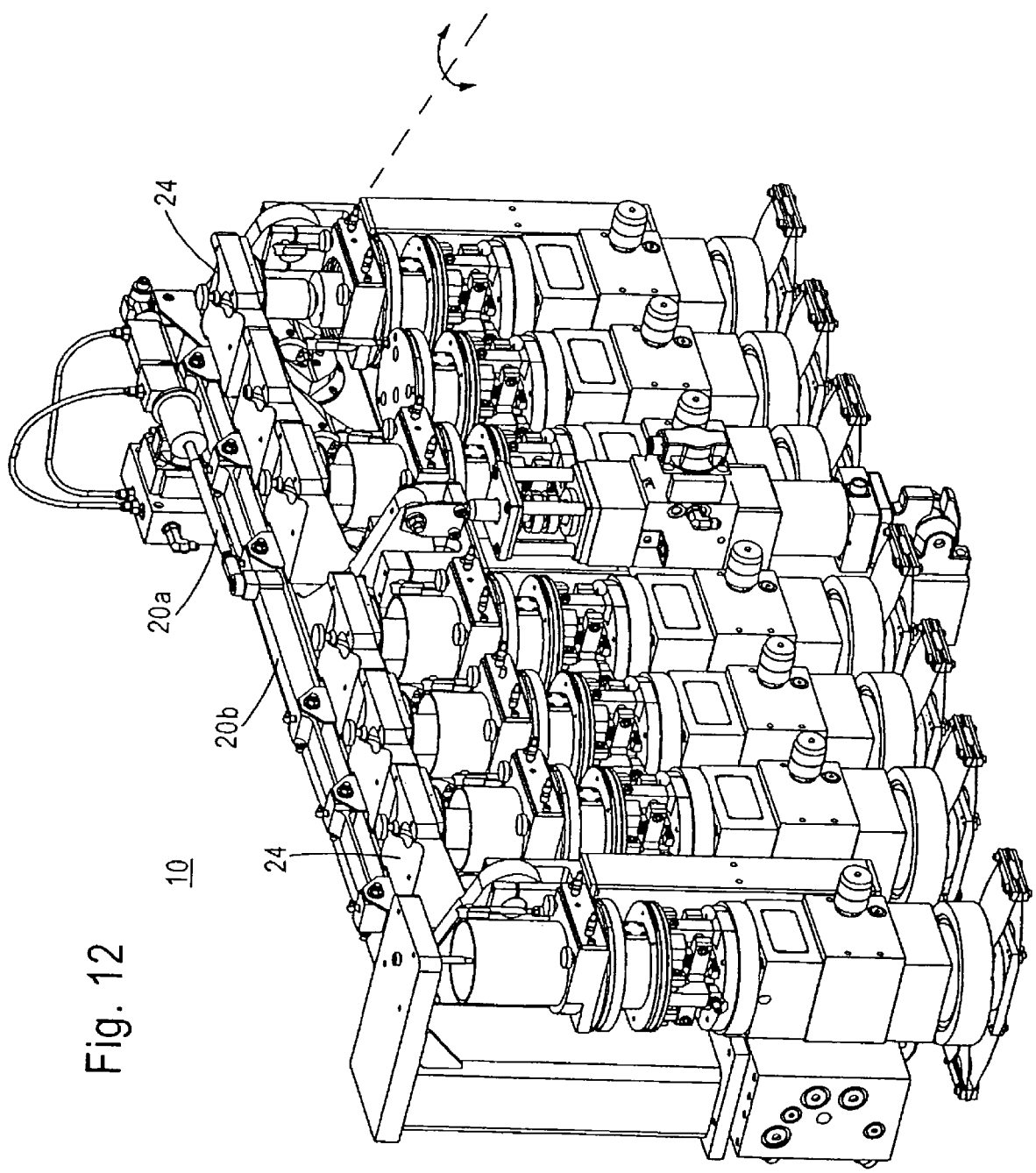
FIG. 12 is a perspective view of the orthopedic simulator of FIG. 1, with an indication of the flexion and extension motion.

FIG. 12 depicts the orthopedic simulator 10 and exemplifies the flexion/extension motion. The linear actuator 20*a* of the linkage 20 extends back and forth in an axial manner, causing the connecting link 20*b* to translate in an axial direction. This causes the inner gimbals 24 at the test stations 12 to move and rotate around an axis of rotation depicted in FIG. 12.

Although not shown, the connecting link 20*b* and connections to the inner gimbals 24 employ high quality bearings, such as long life needle bearings used at key points. The design insures a long life and low lash, creating an accurate machine for a long term use. The low moving mass linkage depicted maximizes performance and is designed for ease of maintenance.

Figure 13:
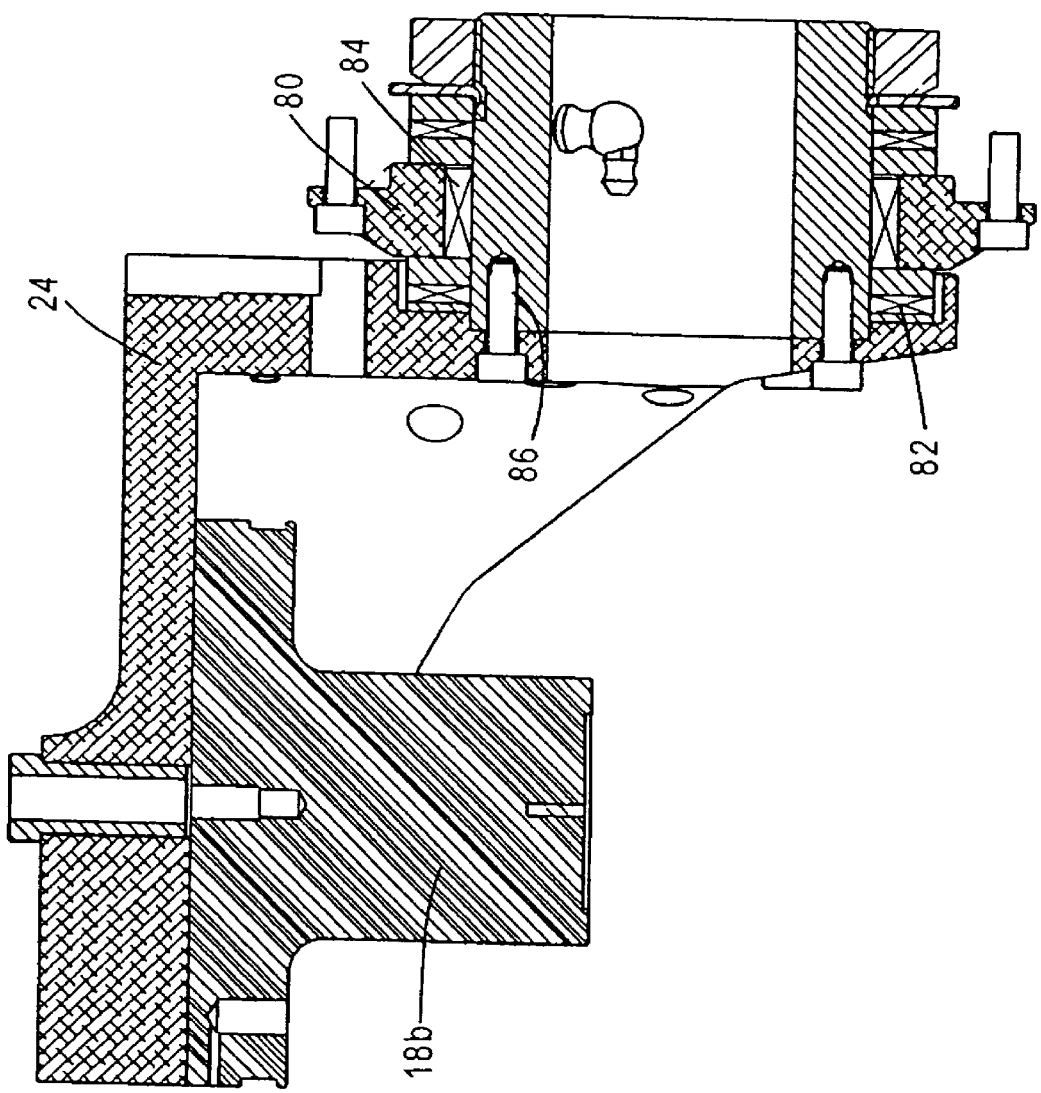
FIG. 13 is a cross-sectional view of a portion of a flexion/extension motion linkage in accordance with embodiments of the invention.

FIG. 13 depicts a cross-sectional portion of the flexion/extension motion linkage. The inner gimbal 24 is depicted as being connected to the upper specimen adapter 18*b*. A stationary bearing housing 80 houses the needle bearings mentioned before. A radial needle bearing 84 is provided, as well as a needle roller thrust bearing 82, which are provided in two places. A tubular shaft 86 permits rotation of the gimbals 24.

Figure 14:
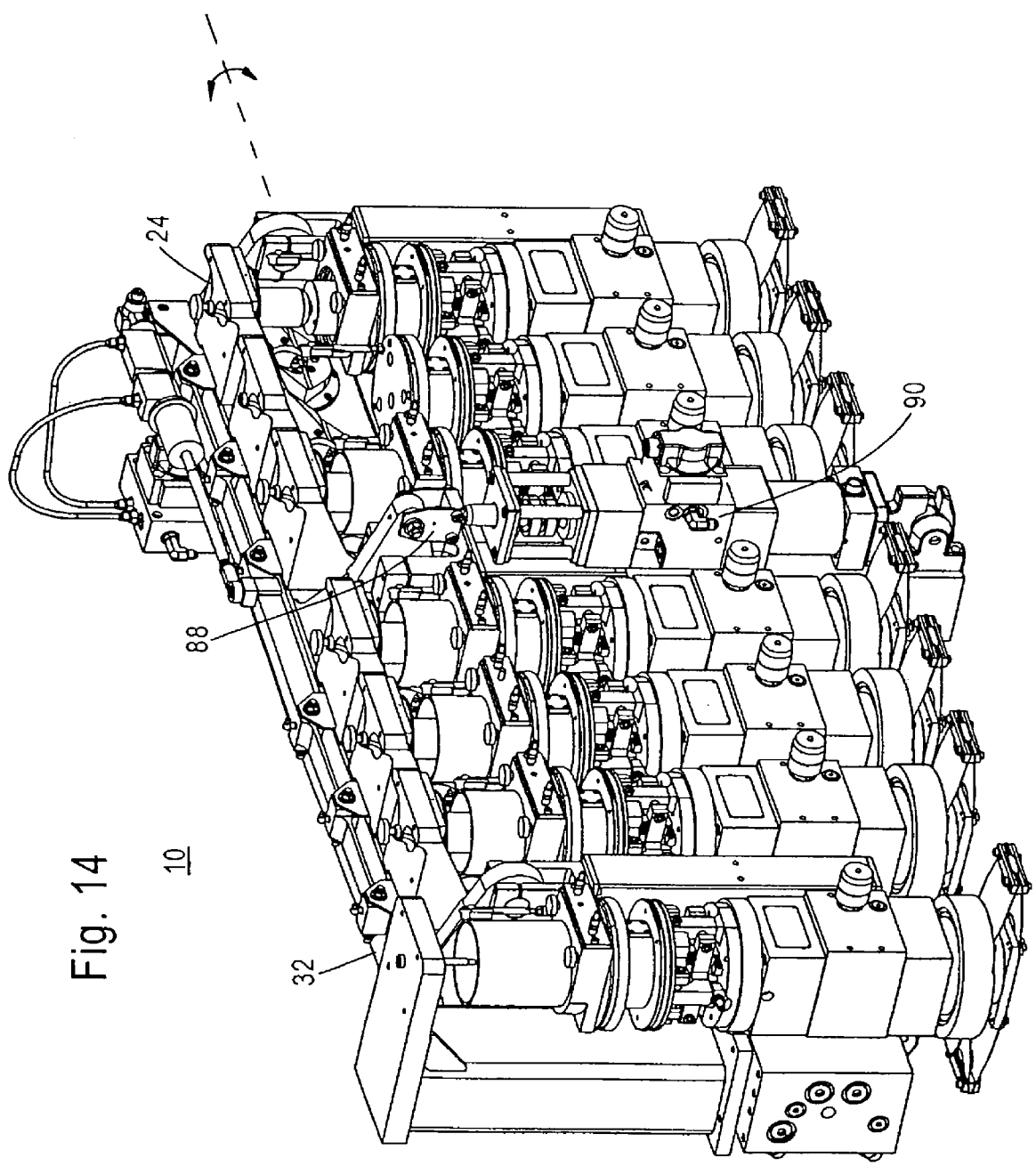
FIG. 14 is a perspective view of the orthopedic simulator of FIG. 1, with an indication of the lateral bending motion around an axis of rotation.

A lateral bending motion around the axis of rotation is depicted in FIG. 14. A moving cross-head 32 (also seen in FIGS. 2*a*-2*d*) is coupled via a connecting link 88 that is moved by linear actuator 90 in an up-and-down motion. This causes the inner gimbals 24 to be pivoted around the axis of rotation.

Figure 15:
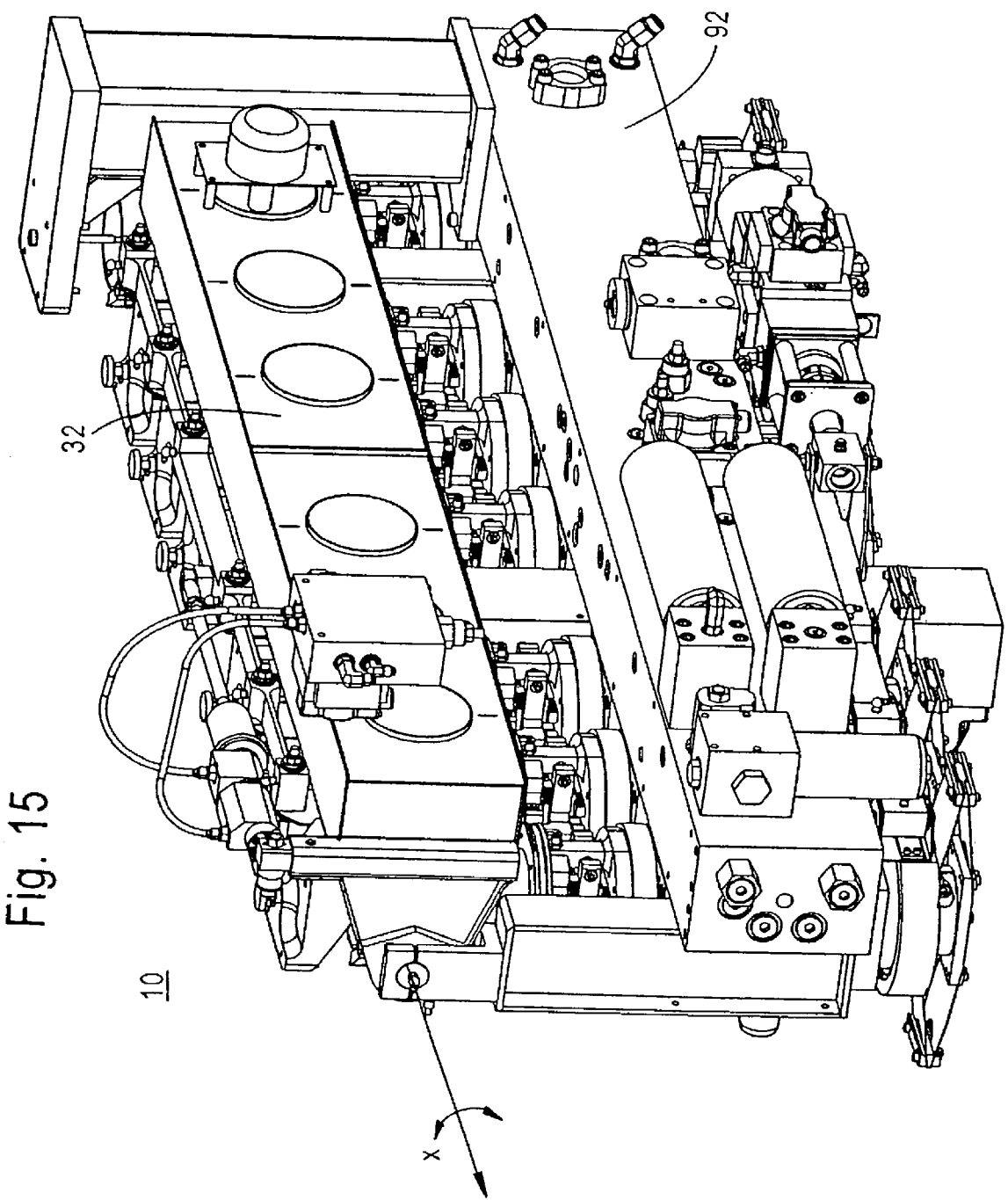
FIG. 15 is a rear perspective view of the orthopedic simulator of FIG. 1.

A rear view of the orthopedic simulator 10 is provided in FIG. 15. The moving cross-head 32 is shown as extending across the orthopedic simulator 10. Also shown in this figure is a central manifold 92, which will be discussed in more detail later. As with the flexion/extension linkages, it is preferred to use long life needle bearings that are of high quality at the key points in the lateral bending motion linkages. These designs ensure long life and low lash, creating an accurate machine for long term use. The low moving mass crosshead assembly maximizes performance. For example, the crosshead assembly 32 may be made of aluminum to provide a very light weight moving mass. In motion, the moving crosshead 32 pivots around the x-axis depicted in FIG. 15.

Figure 16:
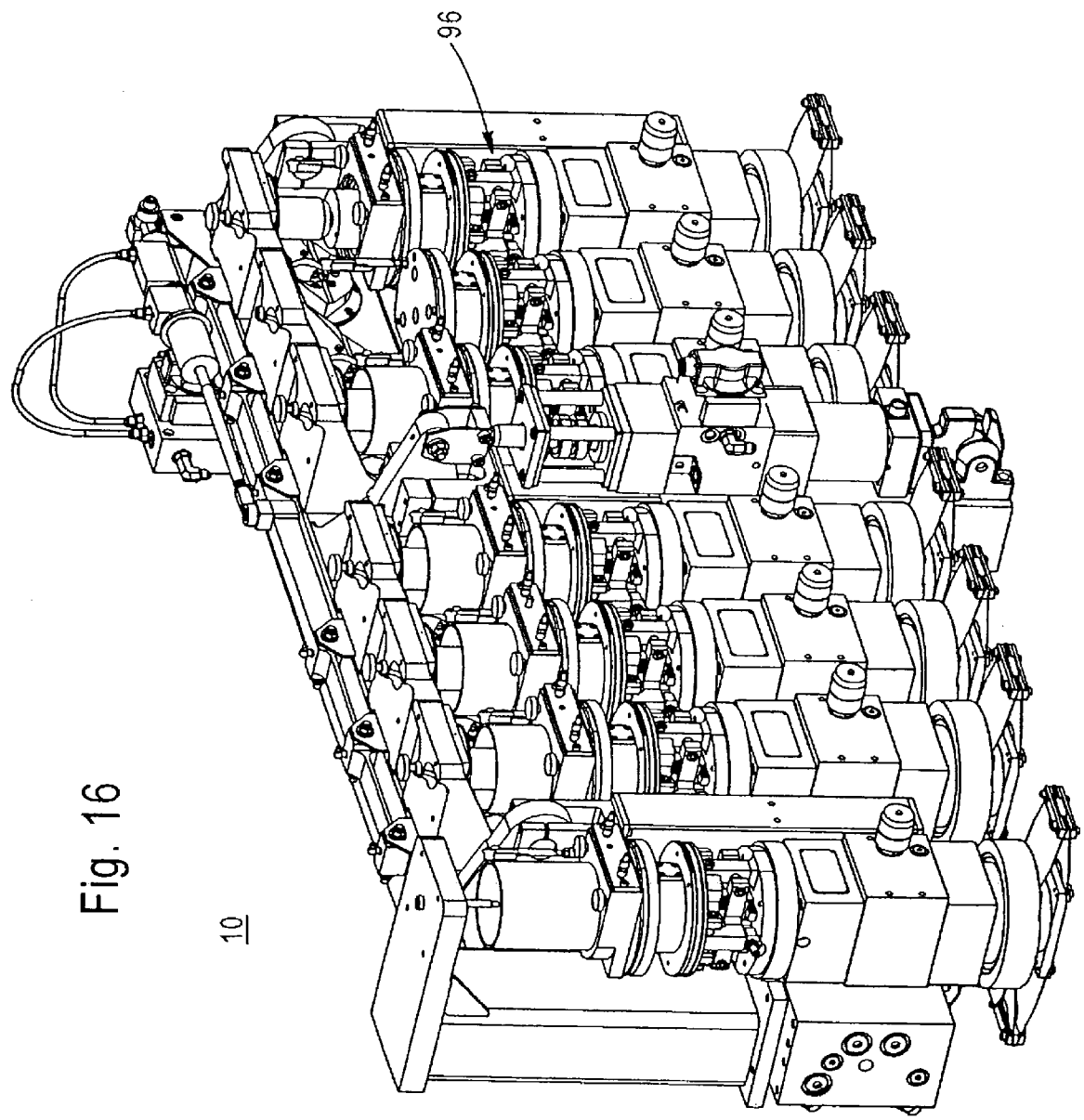
FIG. 16 is a perspective view of the orthopedic simulator of FIG. 1, with an indication of anterior/posterior and lateral translation motions.

FIG. 16 shows the orthopedic simulator and depicts the anterior/posterior and lateral translation motions. A translation stage 96 is illustrated in this drawing. The translation stage includes an x-y slide assembly as will be see in the following figures.

Figure 17:
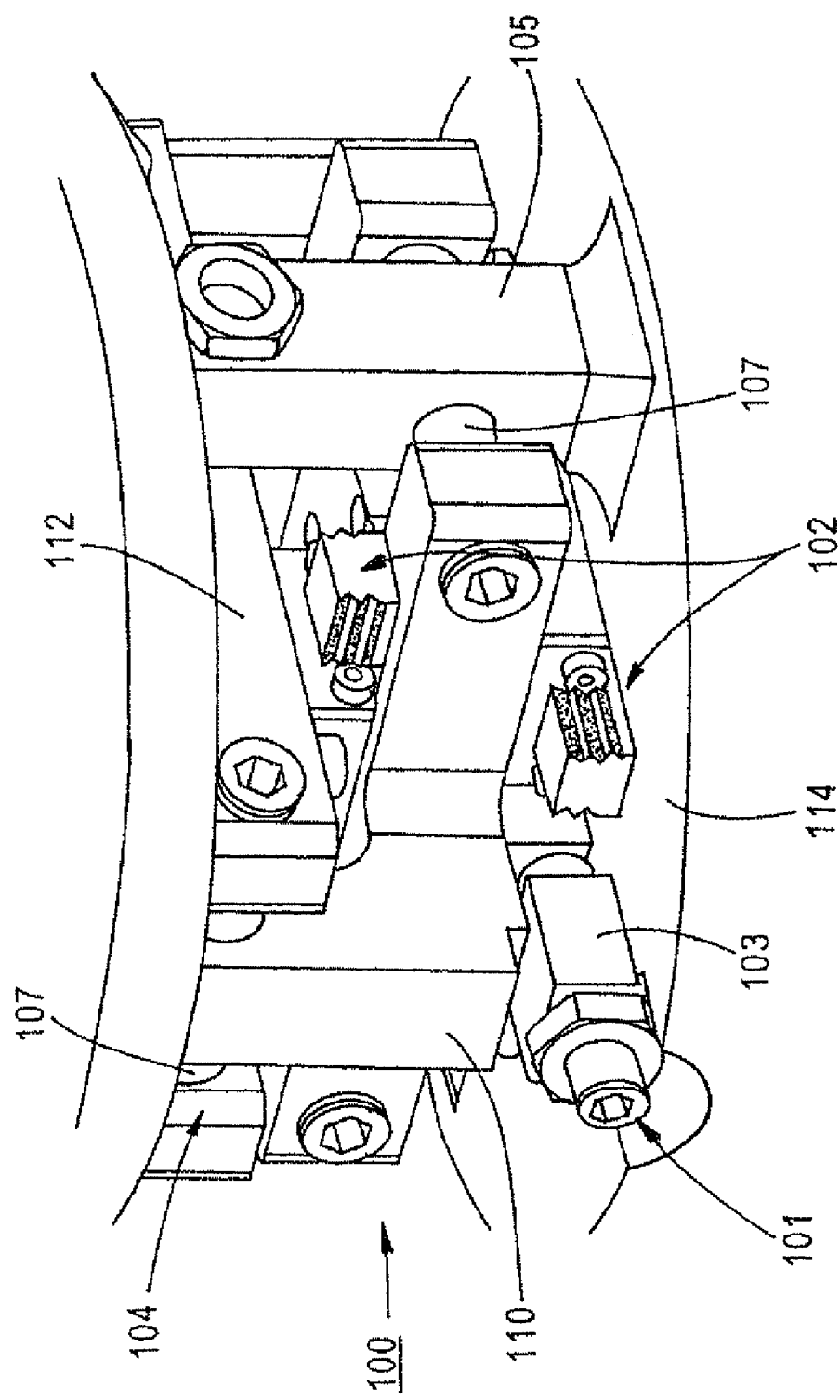
FIG. 17 depicts a portion of an x-y slide assembly in accordance with embodiments of the present invention.

FIG. 17 depicts a portion of the x-y slide assembly 100 that shows linear slides 102 with spaces 104 being provided for springs 107 that produce a biasing force if desired. The springs 107 can be placed between the translation plates 110, 112 themselves, and between the translation plate 110 and certain lock screw posts 105 of the base 114, as will be better appreciated in FIG. 18. The configuration of the x-y slide assembly 100 with springs 107 places the x-y slide assembly 100 into a shear plane loading operational mode.

In other embodiments, the passive control provided by the springs is replaced with an active control by appropriately placed electric, pneumatic or servo-hydraulic actuators (not depicted). For example, such actuators may be provided in the spaces 104. The actuators are controlled in force and/or displacement via an external control system, such as the controller 200. One of the operating modes that is available with such embodiments is shear force control, and another operating mode is shear displacement control.

In the mechanism of the present invention, the Fx and Fy motions and forces take place in the x-y slide assembly 200, when in the spring-loaded configuration described above. An adjustment system allows an operator to set the amount of force in each of the x and y axes. This is not a controlled degree of freedom, but rather, there is free translation if an external force overcomes the spring setting. For spinal implants that are simple ball-in-socket joints located coincident with the Mx, My and Mz centers of the machine, the spring is not engaged. However, some specimens would generate crosstalk loading into the Fx/Fy or Fz axes. This spring constraining force allows a user to simulate the soft tissue surrounding a specimen, or intentionally sideload an implant to simulate mis-implantation. In other embodiments, discussed above, the passive control provided by the springs 107 is replaced by active control through the use of electric, pneumatic or servo-hydraulic actuators.

A first lock screw post 103 on the base 114 receives an adjustable lock screw 101 that is adjusted to interact with the lower translation plate 110. The lock screw 101 allows the x-y slide assembly 100 to be placed in an operational mode that provides for infinite positive axis locking of the slide assembly 100 within a dynamic range. The second lock screw posts 105 also permit locking screws to be received that will interact with the upper translation plate 112 to provide positive axis locking along a different axis from that provided by the lock screw 101.

FIG. 18 is a perspective view of the x-y slide table 100 constructed in accordance with embodiments of the present invention. FIG. 19 shows the x-y slide table 100 in an exploded view. The x-y slide assembly 100 forms a very compact package, with a very light weight assembly. There is a high torsion and shear capability of assembly with high axial dynamic load ratings for each x-y slide assembly 100. Each slide assembly 100 also has high moment load ratings, due to its efficient design. There is an ultra-low coefficient of linear static and dynamic friction provided by the design. Double-row/side miniature roller bearings reduce or eliminate fretting corrosion. Grease may be provided to assist in the elimination of fretting corrosion and further reduce the coefficient of friction and the start up "stiction."

The x-y slide assembly 100 of the present invention may incorporate a number of different modes of operation. These include free-floating to self-center a specimen; a positive axis lock within dynamic range; an ability to produce a large amount of static shear force, on each axis, for simultaneous shear plane loading of specimens; a shear force control and a shear displacement control. The x-axis translation plate has a built-in capability to align the upper specimen tooling and the load cell radially.

The x-y slide assembly 100 of the present invention overcomes particular concerns. For example, other such assemblies in orthopedic simulators used ball bearings in the slide design which lend themselves to fretting and skidding when translating. Other advantages of the present invention include the production of simultaneous transverse shear in a compact design, while producing friction-free stage floating, but yet is infinitely lockable within a dynamic range. The lowest inertia assembly for Mz rotation is produced, at all six test stations 12. The design of the x-y slide assembly 100 can withstand a large amount of lbsF in compression. Further, the x-y slide assembly 100 is a translation assembly that can be easily removed from the Fz actuator 26. It also provides a translation assembly that has over-turning moment capability to react moments caused by side loads that are off-centered loading.

The x-y slide assembly 100 is shown in FIG. 18 in a free-floating configuration, as springs 107 are not provided in the spaces 104, and adjustable lock screws are not provided in the first lock screw post 103 or the second lock screw posts 105. The x-y slide assembly 100 includes the lower translation plate 110 and the upper translation plate 112. In certain embodiments, the lower translation plate 110 translates along the x-axis while the upper translation plate 112 translates along the y axis. The base 114 supports the x-y slide assembly 100 and may be mounted on the load cell depicted earlier. Pins 116 are provided and pressed into base 114 and lower translation plate 110. The pins 116 aid in assembly of the first mounted slide/rail at each axis and ensures squareness of the first rail to the first lock screw post 103, and establish orthogonality between axis platforms, within the limits of the small screw clearances. Screws 118 are provided, as well as pin dowels 120. Linear rail bearings 122 are provided for linear rails 124.

Figure 20:
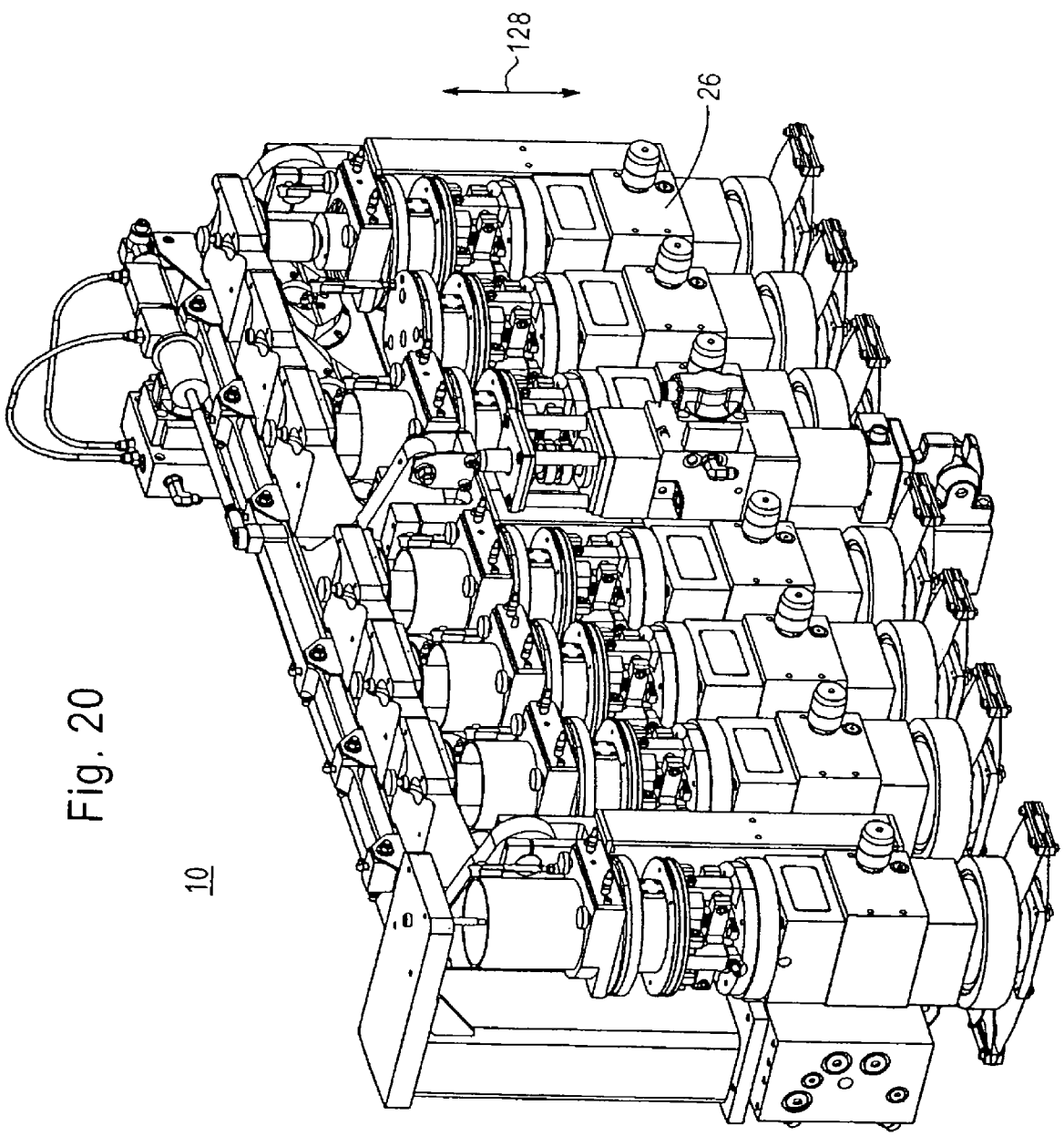
FIG. 20 is a perspective view of the orthopedic simulator of FIG. 1, with an indication of loading in a vertical direction.

FIG. 20 depicts the orthopedic simulator 10 and illustrates the loading in the z direction that is provided in the direction of arrows 128 by the vertical load actuator 26. The integral actuator 26 is integral in nature and may be a precision, seal-less actuator design in certain preferred embodiments. The piston rod is floated on an oil film, and the near zero friction maximizes the load accuracy. A low mass rod may be employed to maximize the performance of axial rotation and vertical load channels. The individual test stations 12 have their own on-off valves. A perspective view of an actuator 26 in isolation is provided in FIG. 21. A top view of the actuator 26 is depicted in FIG. 22 and a side view of the actuator 26 is depicted in FIG. 23. A cross-sectional view of the actuator 26 is depicted in FIG. 24, with an enlargement of a portion from FIG. 24 shown in FIG. 24a.

In certain preferred embodiments, each actuator 26 has a handle 130 on the outside of the actuator 26 that operates a built-in hydraulic valve that allows a user to shut off any station individually. Hence, if a user desires to operate with fewer than six test specimens, or a specimen fails midway through the testing process and it is therefore desirable to remove that specimen from the remainder of the test cycles, the individual test station 12 may be turned off separately from the other test stations 12 without stopping the operation of the machine 10 and the testing of the other specimens. As best seen in FIG. 24, the actuator 26 includes a piston 132 that may be moved axially and rotated. The hydraulic actuator 26 includes a bottom end cap 134 and a top end cap 136. The hydrostatic bearings 138 and 140 are provided. Thrust bearings 142 provide support for a test station 12 when the device is shut off. In such a case, a test station can be removed and the machine operated without the non-operation test station 12 influencing the other test stations 12.

Pressure to extend the piston 132 along the z-axis is provided at port 144, while pressure to retract the piston 132 is provided at port 146.

The hydraulic pressure in return ports 144, 146 are connected to and fed from the central manifold 92 (see FIG. 15) in preferred embodiments. The hydraulic actuator 26 is hydrostatic and is completely without seals, including high-pressure piston seals. The hydrostatic bearings "float" the piston rod and also provide some over-turning moment capabilities. The unique design produces an actuator without seal drag (as in a typical hydraulic actuator), resulting in a device that has extremely low linear and torsional friction. The only friction is the friction that is produced from viscous oil shear. With this design, an equal Fz force is provided across all seven actuators.

Thrust bearings are provided in the end of each end cap 134, 136. The upper end cap 136 has thrust bearings lubricated by a blow-by actuator rod oil leakage. If one specimen should fail before others, an operator can turn off the station 12. The actuator 26 retracts and the assembly will ride on the thrust bearings for a continued Mz motion. The Mz motion is common for all six Fz actuators 26 at the six test stations 12. The seventh test station 14, which operates as a load and soak station for control purposes, is not connected to the Mz drive apparatus.

Figure 26:
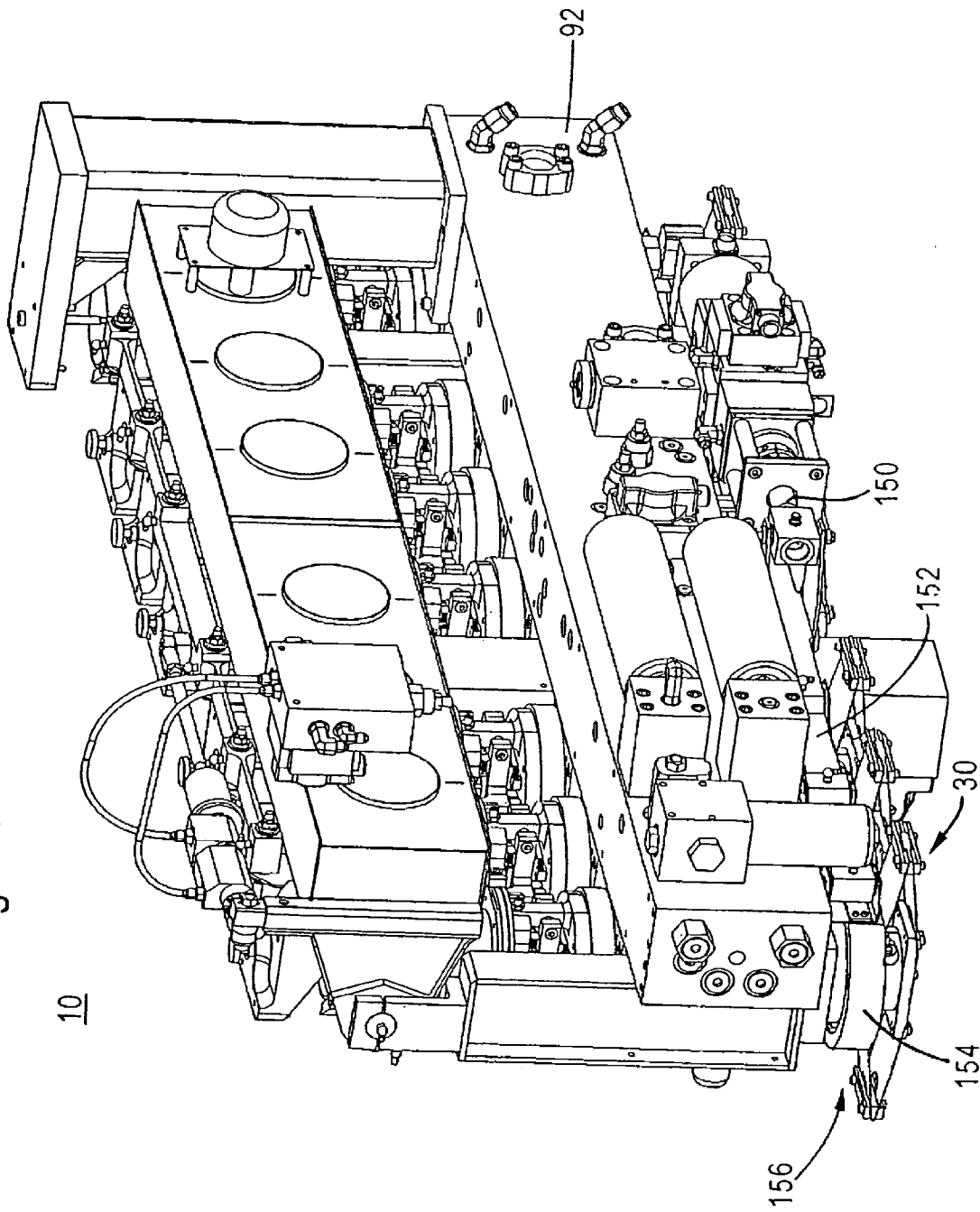
FIG. 26 is a rear perspective view of the orthopedic simulator of FIG. 1, illustrating an embodiment of a central manifold in accordance with embodiments of the present invention.

The central manifold 92, depicted, for example, in FIG. 26, provides an integral manifold for multiple connections and fluid tubing for the orthopedic simulator. The use of a central integral manifold greatly reduces plumbing, provides a performance improvement since there is a greater balancing of fluid and less plumbing is required, a size reduction, a cost reduction and also serves as a structural element. In other words, the central manifold 92 provides a strong cross-brace for the orthopedic simulator 10. Examples of the plumbing include providing the fluid to the extension and retraction fluid connections of the vertical load actuators 26. The central manifold 92 also provides for lubrication fluid circulation.

Figure 25:
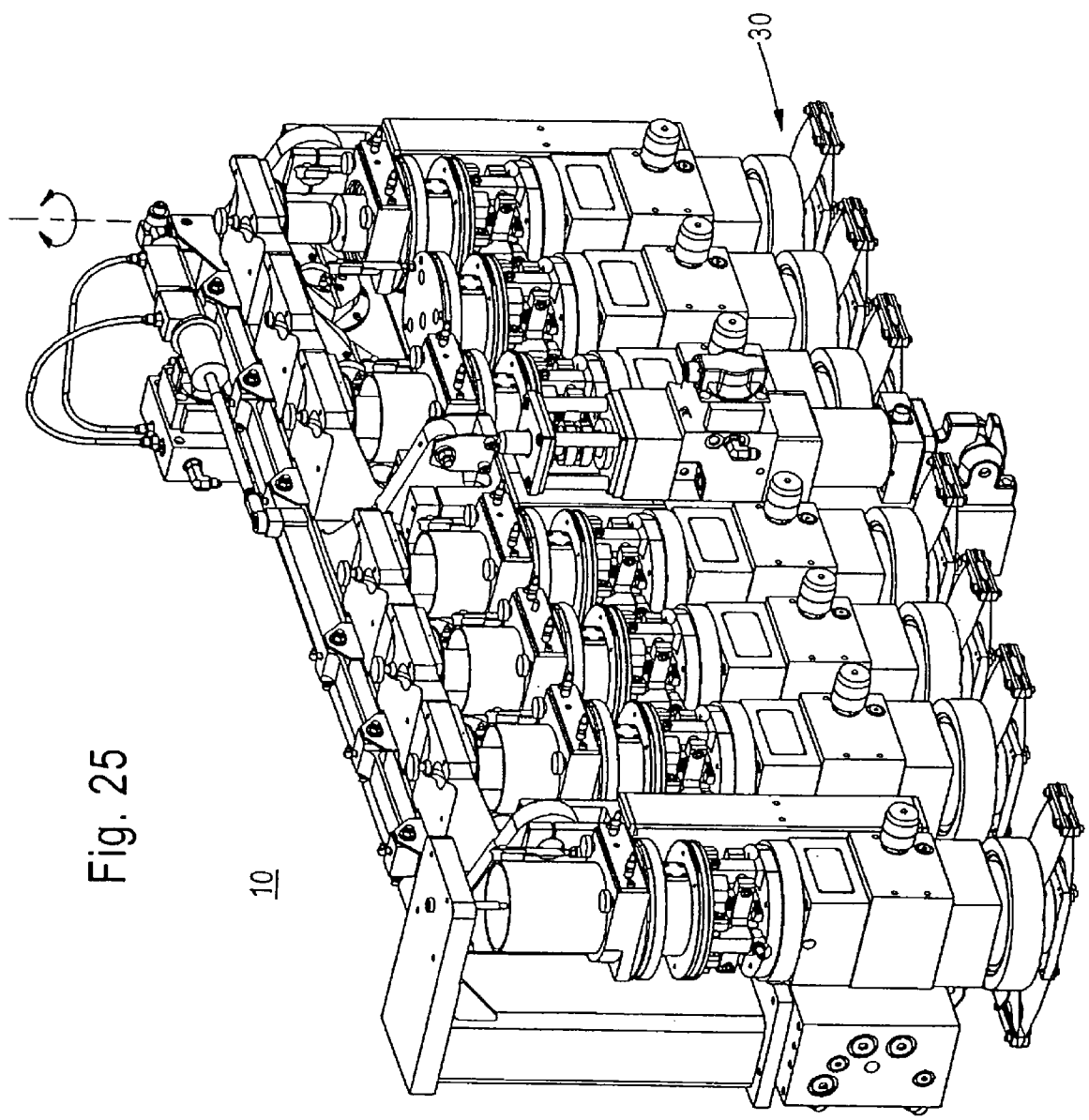
FIG. 25 is a perspective view of the orthopedic simulator of FIG. 1, with an indication of the axial rotation linkage and a moment provided at a test specimen.

FIG. 25 shows the orthopedic simulator 10 and highlights the axial rotation linkage 30 originally shown in FIG. 1. The axial rotation linkage 30 provides a moment Mz at the test specimen. Referring now to FIG. 26, which shows a rear view of the orthopedic simulator 10, a linear actuator 150, via connecting link 152, provides the driving force that causes the axial rotation linkages 30 to rotate around the z-axis.

It is desirable to provide a transmission of drive torque with little deflection related error, having high torsional stiffness. At the same time, low axial stiffness is desirable so that there is little cross-talk onto the vertical loading end and so that cross-talk is not seen at the load cell. The axial rotation linkage includes a rotational transfer link 154 that is coupled to the connecting link 152. Movement of the connecting link 152 in a linear fashion causes the rotational transfer link 154 to freely rotate on bearings around the z-axis. A flexure assembly 156 that is torsionally stiff but axially compliant is coupled to the bottom of the piston 132 of the vertical load actuator 26. The flexure assembly is torsionally stiff so as to rigidly transfer torque between the rotational transfer link 154 and the piston 132 of the actuator 26. A friction free axial/torsion actuation is provided by the combination of the actual rotation linkage 30 and the friction-free vertical force actuator 26. In operation, the vertical load actuator 26 applies a load to the test specimen 40 along the z-axis by moving the piston 132 along the z-axis. Driven by linear actuator 150 through the connecting link 152, the rotational transfer link 154 and the flexure assembly 156 facilitate rigid torque transfer to the piston 132 to the test specimen (not shown) at the test station 12. The piston 132 is allowed to translate along its axis freely due to the high axial compliance provided by the flexure assembly 56 of the axial rotation linkage 30.

Figure 27:
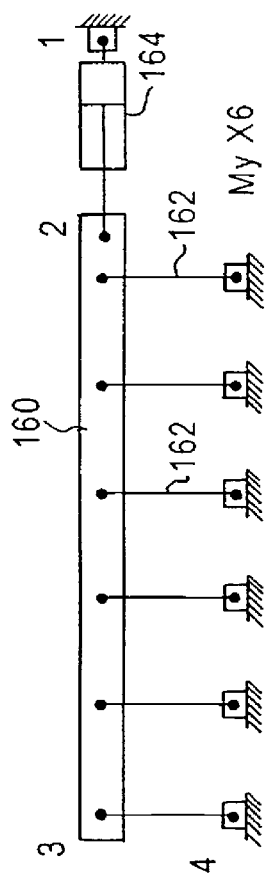
FIGS. 27-29 schematically depict different approaches to linkages.
Figure 28:
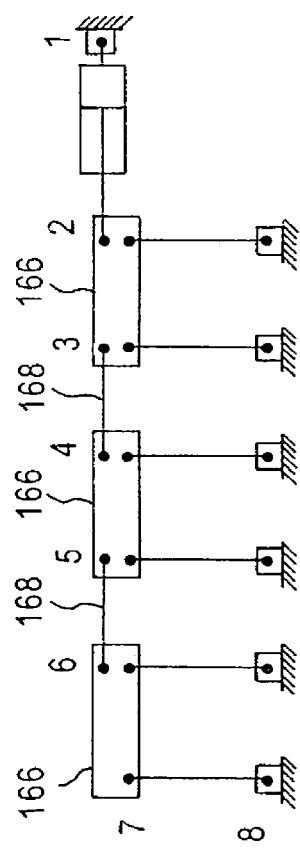
Figure 29:
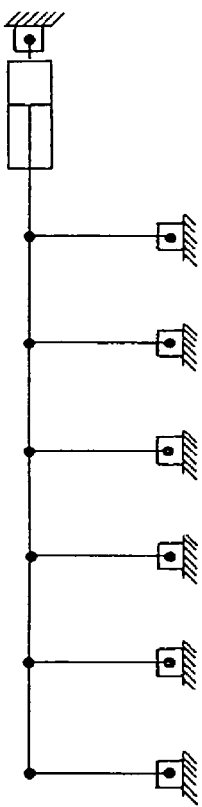

FIGS. 27-29 depict linkage approaches and highlight the differences between embodiments of the present invention and alternate linkage approaches which provide greater joint serialization error. In FIG. 27, a common sublinkage is provided for the flexion/extension (My) and axial rotation (Mz) to thereby create the fewest common number of joints between each specimen, between the displacement measuring device and each specimen, and between the drive actuator and each specimen. In this manner, variability is minimized. The approach provided in the present invention is depicted in FIG. 27. As can be seen, the solid cross-piece 160 provides force to all the linkages 162 at once, from the actuation mechanism 164. By contrast, FIG. 28 employs three separate connecting bars 166 which are connected by two links 168. Hence, those test specimens at the left side of FIG. 28 have a larger number of joints (8) than the number of joints (4) for the left-most specimen in FIG. 27. This increases the variability in the forces and motions applied to the test specimens from test station 12 to test station 12. A similar variability is provided in FIG. 29, in which a large number of joints are provided for the various test stations, with each test station having a different number of joints. Hence, the arrangement of the present invention reduces variability in force and motion application from station 12 to station 12.

Figure 30:
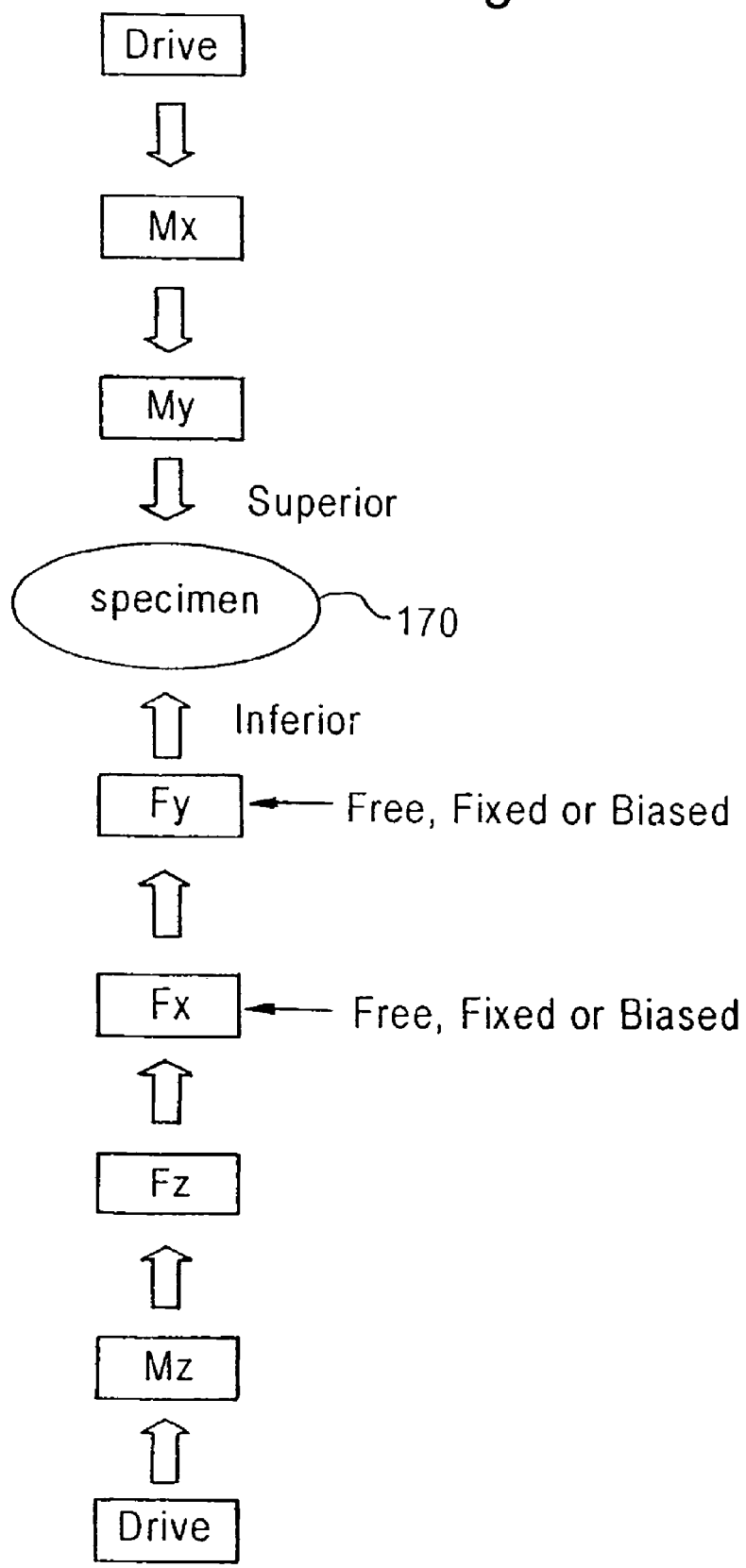
FIG. 30 schematically depicts a nesting order of forces in accordance with embodiments of the present invention.

FIG. 30 schematically depicts the nesting order of forces in accordance with embodiments of the present invention. This nesting order of forces is achieved by the arrangement of the linkages as depicted in the figures throughout this application.

The mechanism system generates relative motions and forces between the lower (inferior) and upper (superior) portions of orthopedic devices, such as multiple intervertebral disc implants, simultaneously to generate wear on the artificial bearing surfaces over similar motion and force induced degradation with time. The mechanism applies these motions and forces in such a way as to maximize the accuracy, test speed and durability of the linkage. The full six degree of freedom linkage system is nested as shown in FIG. 30 to maximize performance and accuracy. Typical spinal implant tests in conventional systems require higher displacements in the flexion/extension direction (My), as compared to the lateral bending (Mx) and axial rotation (Mz) rotations. These motions are often performed at a common or similar frequency and wave shapes. Therefore, the flexion/extension motion represents the most demanding performance. The mechanism system of the present invention is nested, however, so as to place the sub-mechanism with the highest required performance closest to the specimen. This thereby minimizes the moving mass and any related inertial induced error. Hence, as seen in FIG. 30, the schematically induced specimen is indicated by reference numeral 170. The closest sub-mechanism to the superior (upper) portion of the test specimen 170 is the flexion/extension (My). The lateral bending (Mx) is further from the superior portion of the specimen 170, as indicated by FIG. 30. Finally, the drive for the Mx and My forces is furthest away from the specimen 170. For the lower (or inferior) portion of the specimen 170, the force in the y direction is free, fixed or biased and has a minimized moving mass and has the highest required performance. The forces in the x direction Fx is then nested further from the specimen 170 than the Fy force. The vertical force provided by the actuator 26, Fz, is still further from the inferior portion of the test specimen 170, with the moment around the z-axis, Mz, being provided in a nesting arrangement still further from the test specimen 170. The drive for all these forces is provided as indicated.

The Euler sequence of rotational motion as applied by the mechanism of the present invention is flexion/extension→lateral bending→axial rotation. In the field of testing of spinal implants, this ordering of the mechanism promotes maximum performance and minimizes the additive joint error. The independency of linkages reduces or eliminates cross-talk and allows accurate control of the phases between the individual mechanisms. This is important to create the desired and controlled loading of the test specimen 170.

Figure 31:
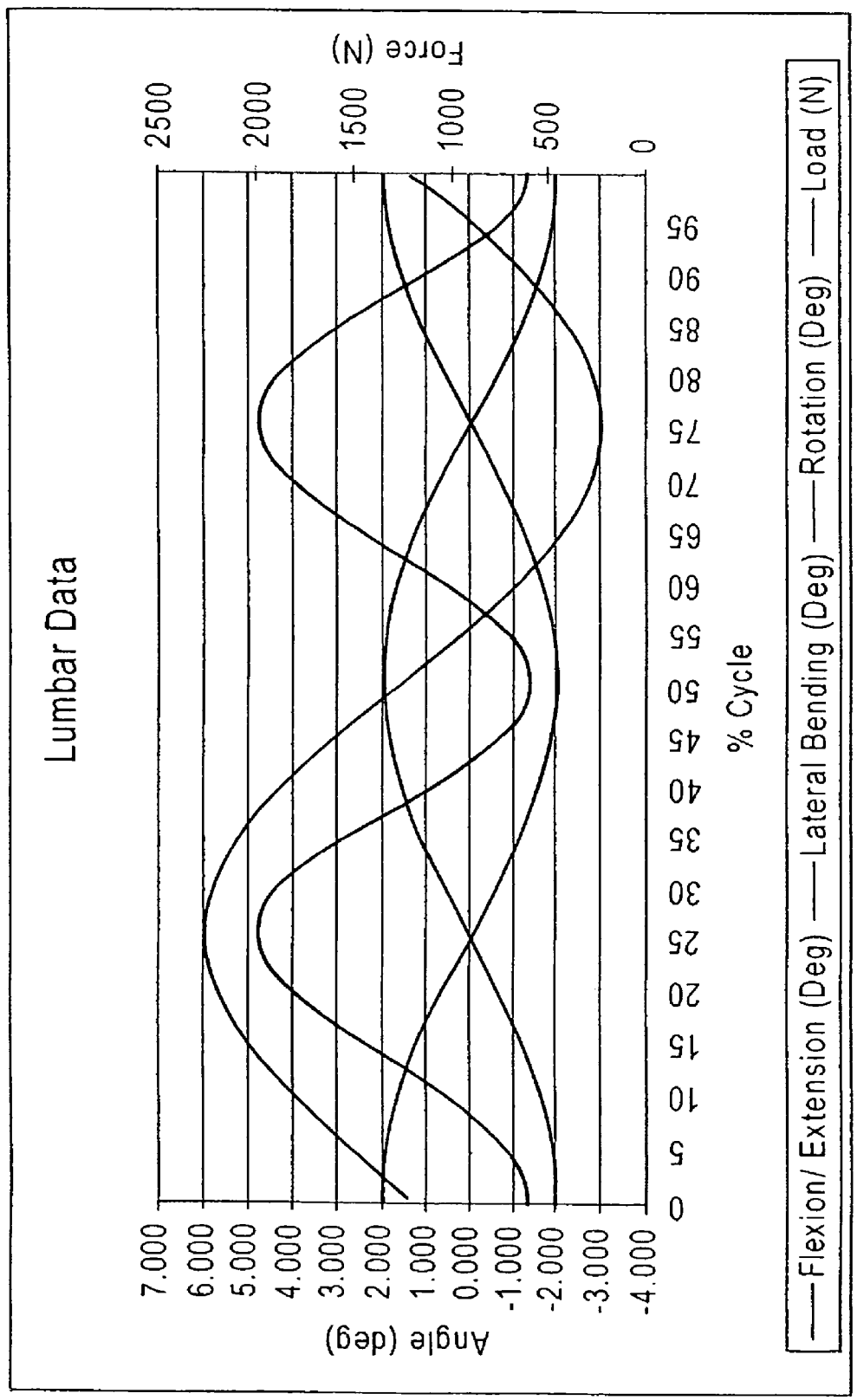
FIG. 31 shows the required forces for application to a test specimen intended for a lumbar region according to an exemplary set of curves.
Figure 32:
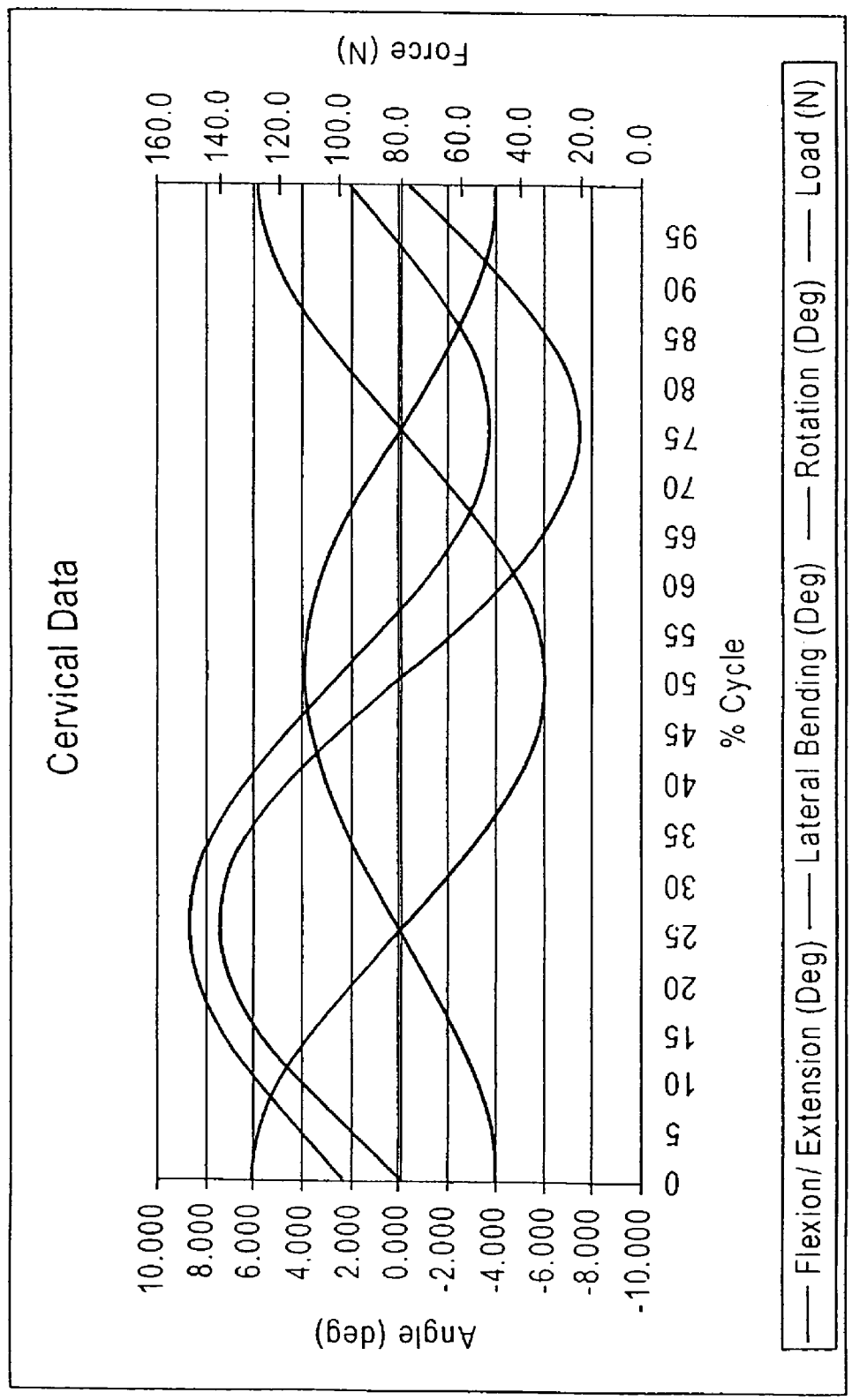
FIG. 32 shows the same information as FIG. 31, but for cervical data.
Figure 33:
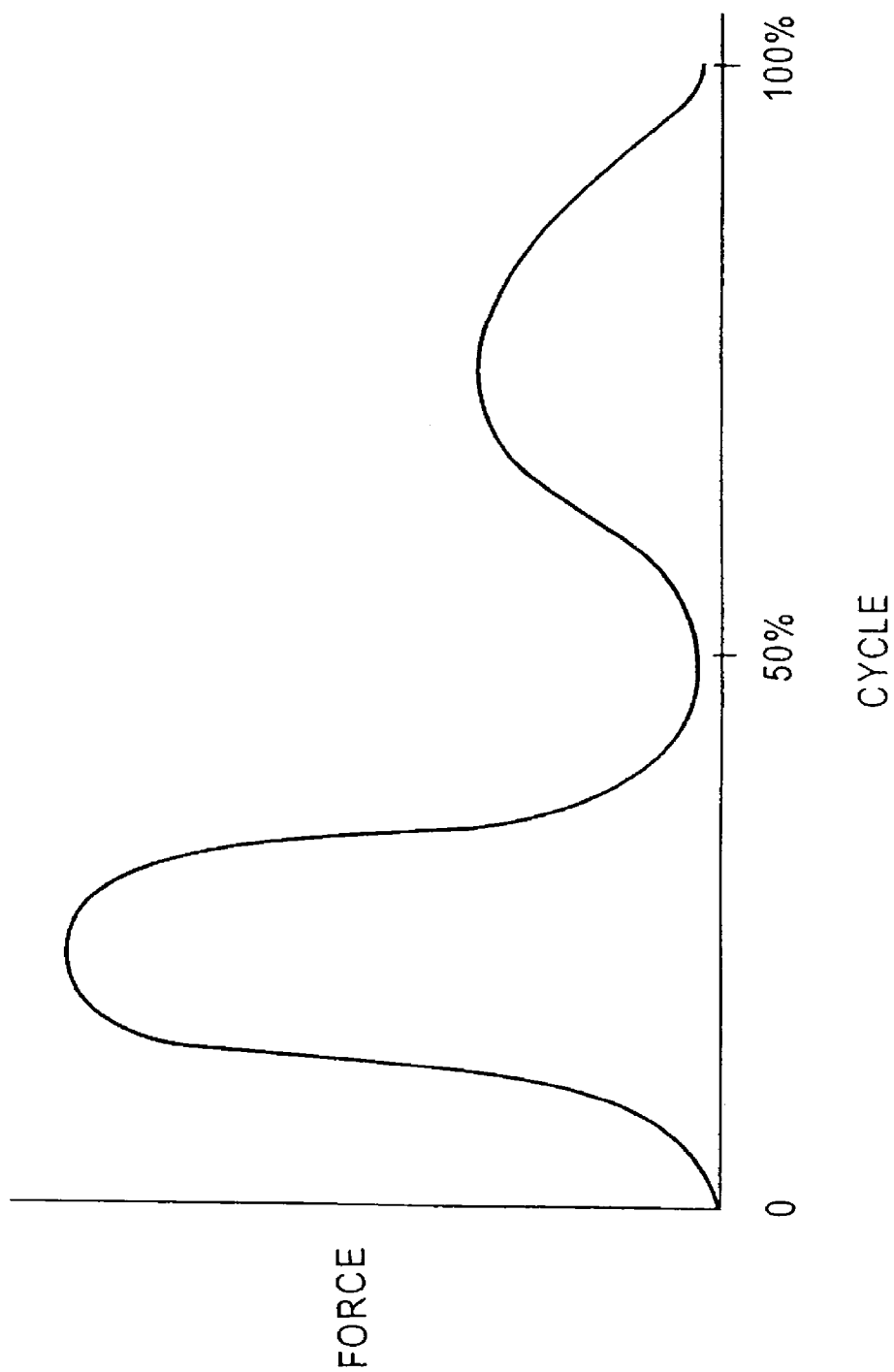
FIG. 33 shows curves for non-sinusoidal input data in accordance with exemplary embodiments of the invention.

FIG. 31 shows the required forces for applying to a test specimen of a spinal implant intended for the lumbar region according to the an exemplary set of curves. Similarly, FIG. 32 shows the same information for cervical data. Duty cycle loading involves inserting high loads and displacement activity into a more typical repeating activity, such as lifting a heavy box periodically. This allows for the insertion of periodic overload states. Such overload states are known to potentially induce damage, but are relatively rare so that their rarity should be considered and the overload states placed in the context of other daily activity when included. In addition to duty cycle loading, embodiments of the present invention provide for re-creating any sinusoidal or non-sinusoidal curve, which allows for more accurate simulation (e.g., a "walking simulation"). The embodiments of the invention allow for inputting non-sinusoidal data with varying phase, amplitude and frequency content, such as real walking profiles. These curves, such as shown in FIG. 33, can be repeated for a large number of cycles, and hence are fatigue or wear generating. The representation of activity is not limited to walking, as one of ordinary skill in the art will readily appreciate, but may be used to simulate any number of replicated activities in a serial or repetitive fashion. Accordingly, a controller 200, seen only in FIG. 1, is used to independently and individually control each of the motion devices. Hence, the flexion/extension, lateral bending, rotation, and loading of the test specimen 170 may be controlled to any desirable curve through the use of control software and the mechanisms provided in the orthopedic simulator 10. This allows for the testing of an orthopedic device that simulates actual conditions that the orthopedic device will be subjected to rather than the constant forces depicted in FIGS. 31 and 32 applied over 10 million cycles. For example, a test may account for the typical day for humans. Such a day may include sitting for hours at a time with intermittent periods of activity, including walking and sleeping periods. Strenuous physical activity, such as for athletes, may also be better modeled. The controller 200 thereby more accurately causes the orthopedic simulator 10 to simulate the forces that a spinal implant or other orthopedic device will actually be expected to see for a typical implant recipient.

FIG. 34 depicts the orthopedic simulator 10 within a housing 178. The use of a housing 178 prevents contamination and reduces oil within the environment. Switches 180 allow a test station to be shut down very quickly in order to prevent invalidating of a test if an individual test station 12 should experience difficulty in operation.

The embodiments of the present invention described above provide an orthopedic simulator with a temperature control arrangement for maintaining a specimen bath at a precise temperature, without subjecting the bath fluid to potential over-temperature fluid degradation. Stability and consistency are provided in certain embodiments, as well as cost savings due to use of a single heater and controller.

Although the present invention has been described and illustrated in detail, it is to be clearly understood that the same is by way of illustration and example only and is not to be taken by way of limitation.

What is claimed is:

1. An orthopedic simulator comprising:
   a holder assembly configured to hold a test specimen; and
   a multi-axis slide table coupled to the holder assembly, the multi-axis slide table including:
   a base;
   a first translation plate mounted to the base through a first linear slide and rail arrangement and movable along a first axis;
   a second translation plate mounted to the first translation plate through a second linear slide and rail arrangement and movable along a second axis different from the first axis; and
   at least one post coupled to the base and having a screw slot configured to receive a lock screw and the lock screw being position in alignment with one of the first or second translation plates to provide a positive lock to limit movement of the one of the first or second translation plates.

2. The simulator of claim 1 comprising one or more springs configured to supply a force relative to at least one of the first or second translation plates to provide a load input to the test specimen.

3. The simulator of claim 2, comprising a plurality of springs to supply the force to each of the first and second translation plates along the first and second axes.

4. The simulator of claim 1 comprising one or more actuators coupled to at least one of the first or second translation plates that produce at least one of a static or dynamic shear force on the at least one of the first or second translation plates.

5. The simulator of claim 4, wherein the one or more actuators include at least one of an electric actuator, a pneumatic actuator or a servo-hydraulic actuator.

6. The simulator of claim 1, wherein the first and second linear slide and rail arrangements include double row/side roller bearings.

7. The simulator of claim 1, further comprising a soft tissue simulating arrangement coupled to the first and second translation plates.

8. The simulator assembly of claim 1, comprising a free-floating mode and a positive lock mode wherein in the positive lock mode the lock screw is aligned to limit movement of the one of the first or second translation plates.

9. The simulator of claim 1 comprising a plurality of posts spaced along at least one of the first or second axes and each of the plurality of posts configured to receive lock screws to provide the positive lock to limit movement of the one of the first or second translation plates along the first or second axis.

10. The simulator of claim 9 wherein the plurality of posts include first and second posts coupled to the base and configured to receive the lock screws to provide the positive lock to limit movement of the first translation plate along the first axis and third and fourth posts coupled to the base and configured to receive the lock screws to provide the positive lock to limit movement of the second translation plate along the second axis.

11. The simulator of claim 10 wherein the first and second axes are generally transverse and the first and second posts are spaced along the first axis and the third and fourth posts are spaced along the second axis generally transverse to the first axis.

12. The simulator of claim 10 wherein the third and fourth posts include a slot therethrough and comprising rods coupled to the first translation plate and movable along the slot of the third and fourth posts for movement of the first translation plate along the first axis and the first translation plate including upright portions having a slot therethrough and comprising rods coupled to the second translation plate and moveable along the slot of the upright portions for movement of the second translation plate along the second axis.

13. The simulator of claim 12 and comprising a spring between the third and fourth posts and the first translation plate and another spring between the upright portions and the second translation plate.

14. The simulator of claim 9 wherein the lock screws are adjustable to adjust a positive lock position along the first or second axis.

15. The simulator of claim 1 wherein the holder assembly includes first and second holders or adapters and the slide table is coupled to one of the first or second holders and comprising one or more actuators coupled to the other of the first or second holders.

16. A simulator assembly comprising:
a base;
a holder assembly configured to hold a test specimen;
a first translation plate coupled to the base through a first linear slide and rail arrangement and movable along a first axis;
a second translation plate coupled to the first translation plate through a second linear slide and rail arrangement and movable along a second axis, different from the first axis;
at least one post coupled to the base;
at least one upright portion coupled to the first translation plate;
a first spring assembly configured to input a first biasing force to the first translation plate and the first spring assembly includes a spring between the at least one post and the first translation plate to input the first biasing force; and
a second spring assembly configured to input a second biasing force to the second translation plate and the second spring assembly includes a spring between the at least one upright portion and the second translation plate to input second the biasing force.

17. The assembly of claim 16, wherein the first and second linear slide and rail arrangements include double row/side roller bearings.

18. The assembly of claim 16 including a first rod coupled to the first translation plate and a second rod coupled to the second translation plate wherein the at least one post and the at least one upright portion include a slot therethrough and the first rod is movable through the slot of the at least one post and the second rod is movable through the slot of the at least one upright portion.

19. The assembly of claim 18 and comprising a plurality of posts coupled to the base and a plurality of upright portions coupled to the first translation plate and including a plurality of first rods coupled to the first translation plate and movable through first slots of the plurality of posts coupled to the base and a plurality of second rods coupled to the second translation plate and moveable through second slots of the plurality of upright portions.

20. The assembly of claim 19 wherein each of the first and second translation plates include pairs of arms and the plurality of first and second rods are coupled between the pairs of arms on the first and second translation plates.

21. The assembly of claim 19 wherein the plurality of upright posts include openings configured to receive lock screws to provide a positive lock to limit stroke of the second translation plate along the second axis.

22. The assembly of claim 19 wherein the base includes lock screw openings configured to receive lock screws to provide a positive lock to limit stroke of the first translation plate along the first axis.

23. The assembly of claim 16 wherein the holder assembly comprises first and second holders to hold the test specimen therebetween and the first and second translation plates are coupled to the first holder and comprising at least one actuator coupled to the first holder and configured to supply a load force to the test specimen through the first and second translation plates.

24. An orthopedic simulator comprising:
a holder assembly configured to hold a test specimen;
a multi-axis slide table coupled to the holder assembly, the multi-axis slide table including:
a first translation plate mounted to a base through a first linear slide and rail assembly and movable along a first axis;
a second translation plate mounted to the first translation plate through a second linear slide and rail assembly and movable along a second axis different from the first axis; and
a soft tissue simulating arrangement coupled to the first and second translation plates to simulate forces or input from soft tissue.

25. The simulator of claim 24 wherein the soft tissue simulating arrangement comprises a plurality of springs to provide a biasing force to simulate the forces or input from the soft tissue.

26. The simulator of claim 25 wherein the plurality of springs includes at least one spring configured to supply a first biasing force relative to the first translation plate along the first axis and at least one spring configured to supply a second biasing force relative to the second translation plate along the second axis.

27. The simulator of claim 25 wherein the holder assembly comprises first and second holders to hold the test specimen therebetween and the first and second translation plates are coupled to the first holder and comprising at least one actuator coupled to the first holder and configured to supply a load force to the test specimen through the first and second translation plates.

28. The simulator of claim 27 and comprising at least one actuator coupled to the second holder and configured to supply another load force to the test specimen through the second holder.

* * * * *